US012710431B2

(12) United States Patent
Adams et al.

(10) Patent No.: US 12,710,431 B2
(45) Date of Patent: Aug. 18, 2026

(54) DIAGNOSTIC FOR CHILDHOOD RISK OF AUTISM SPECTRUM DISORDER

(71) Applicants: Arizona Board of Regents on Behalf of Arizona State University, Tempe, AZ (US); Rensselaer Polytechnic Institute, Troy, NJ (US)

(72) Inventors: James B. Adams, Tempe, AZ (US); Juergen Hahn, Troy, NJ (US); Haiwei Gu, Tempe, AZ (US)

(73) Assignees: Arizona Board of Regents on Behalf of Arizona State University, Tempe, AZ (US); Rensselaer Polytechnic Institute, Troy, NY (US)

( * ) Notice: Subject to any disclaimer, the term of this patent is extended or adjusted under 35 U.S.C. 154(b) by 1175 days.

(21) Appl. No.: 17/601,235

(22) PCT Filed: Apr. 6, 2020

(86) PCT No.: PCT/US2020/026912

§ 371 (c)(1),
(2) Date: Oct. 4, 2021

(87) PCT Pub. No.: WO2020/206444

PCT Pub. Date: Oct. 8, 2020

(65) Prior Publication Data

US 2022/0214358 A1 Jul. 7, 2022

Related U.S. Application Data

(60) Provisional application No. 62/830,043, filed on Apr. 5, 2019.

(51) Int. Cl.
*G01N 33/68* (2006.01)

(52) U.S. Cl.
CPC ..... *G01N 33/6896* (2013.01); *G01N 2570/00* (2013.01); *G01N 2800/28* (2013.01)

(58) Field of Classification Search
CPC ........... G01N 33/6896; G01N 2570/00; G01N 2800/28; G01N 33/50; A61P 25/22
See application file for complete search history.

(56) References Cited

U.S. PATENT DOCUMENTS

| | | | |
|---|---|---|---|
| 2012/0122969 | A1 | 5/2012 | Miller |
| 2013/0005806 | A1 | 1/2013 | Beaudet et al. |

FOREIGN PATENT DOCUMENTS

| | | | |
|---|---|---|---|
| WO | 2014036182 | A2 | 3/2014 |
| WO | 2015006160 | A2 | 1/2015 |
| WO | 2015181391 | A1 | 12/2015 |
| WO | 2017197252 | A1 | 11/2017 |
| WO | 2018089794 | A1 | 5/2018 |

OTHER PUBLICATIONS

Abu-Akel et al., Mind the prevalence rate: overestimating the clinical utility of psychiatric diagnostic classifiers, Psychological Medicine, 48, 1225-1227, 3 pages, 2017.

Fein et al., Optimizing Outcome in Autism Spectrum Disorders, Policy Insights from the Behavioral and Brain Sciences vol. 4(1), 71-78, 2017.

Adams et al., Significant Association of Urinary Toxic Metals and Autism-Related Symptoms—A Nonlinear Statistical Analysis with Cross Validation, PLoS ONE 12(1), 24 pages, 2017.

Adams et al., Gastrointestinal flora and gastrointestinal status in children with autism-comparisons to typical children and correlation with autism severity, BMC Gastroenterology 2011, 11:22, 13 pages, 2011.

Fisher, The use of multiple measurements in taxonomic problems, The Annals of Human Genetics, 11 pages, 1936.

Fletcher-Watson et al., The potential of eye-tracking as a sensitive measure of behavioural change in response to intervention, Scientific Reports 8:14715, 7 pages, 2018.

French et al., Annual Research Review: Early intervention for infants and young children with, or at-risk of, autism spectrum disorder: a systematic review, The Journal of Child Psychology and Psychiatry, 59:4, 13 pages, 2018.

Frye et al., Approaches to studying and manipulating the enteric microbiome to improve autism symptoms, Microbial Ecology in Health and Disease, 15 pages, 2015.

Gaugler et al., Most genetic risk for autism resides with common variation, Nature Genetics, 7 pages, 204.

Holingue et al., Gastrointestinal Symptoms in Autism Spectrum Disorder: A Review of the Literature on Ascertainment and Prevalence, Autism Research 11:24-36 13 pages, 2018.

Howsmon et al., Classification and adaptive behavior prediction of children with autism spectrum disorder based upon multivariate data analysis of markers of oxidative stress and DNA methylation, PLoS Computational Biology 13(3): e1005385, 15 pages, 2017.

Howsmon et al., Multivariate techniques enable a biochemical classification of children with autism spectrum disorder versus typically-developing peers: A comparison and validation study, AIChE Bioengineering & Translational Medicine, 10 pages, 2018.

Kang et al., Microbiota Transfer Therapy alters gut ecosystem and improved gastrointestinal and autism symptoms: an open-label study, Microbiome 5:10, 16 pages, 2017.

Krajmalnik-Brown et al., Gut bacteria in children with autism spectrum disorders: challenges and promise of studying how a complex community influences a complex disease, Microbial Ecology in Health and Disease, 9 pages, 2015.

Li et al., The microbiota-gut-grain axis and its potential therapeutic role in autism spectrum disorder, Neuroscience 324: 131-139, 9 pages, 2016.

Mandy et al., Annual Research Review: The role of the environment in the developmental psychopathology of autism spectrum condition, Journal of Child Psychology and Psychiatry 57:3, 22 pages, 2016.

(Continued)

*Primary Examiner* — Olga N Chernyshev
(74) *Attorney, Agent, or Firm* — Polsinelli PC

(57) ABSTRACT

Provided herein are methods of obtaining and applying measurements of metabolites to diagnosing ASD in a subject, particularly children, with high specificity and sensitivity. The metabolites can be measured in urine, serum, and whole blood samples.

12 Claims, 3 Drawing Sheets

(56) References Cited

OTHER PUBLICATIONS

Choi et al., Metabolomics of mammalian brain reveals regional differences, BMC Systems Biology 2018, 12(Supl 8):127, 12 pages, 2018.
McPartland, Considerations in biomarker development for neurodevelopmental disorders, Curr Opin Neurol, 29(2), 9 pages, 2016.
Murias et al., Validation of Eye-Tracking Measure of Social Attention as a Potential Biomarker for Autism Clinical Trials, Autism Research 11:161-174, 9 pages, 2018.
Orinstein et al., Intervention History of Children and Adolescents with High-Functioning Autism and Optimal Outcomes, J Dev Behav Pediatr, 35(4): 247-256, 18 pages, 2014.
Pierce et al., To Screen or Not to Screen Universally for Autism is not the Question: Why the Task Force Got It Wrong, The Journal of Pediatrics, 13 pages, 2016.
Baio et al., Prevalence of Autism Spectrum Disorder Among Children Aged 8 Years—Autism and Developmental Disabilities Monitoring Network, 11 Sites, United States, 2014, Surveillance Summaries, 28 pages, 2014.
Ryberg, Evidence for the Implementation of the Early Start Denver Model for Young Children With Autism Spectrum Disorder, Journal of the American Psychiatric Nurses Associate, vol. 21(5) 327-337, 11 pages, 2015.
Soke et al., Prevalence of Co-occurring Medical and Behavioral Conditions/Symptoms Among 4- and 8-Year-Old Children with Autism Spectrum Disorder in Selected Areas of the United States in 2010, Journal of Autism and Developmental Disorders 48:2663-2676, 14 pages, 2018.
Vargason et al., On the Use of Multivariate Methods for Analysis of Data from Biological Networks, Processes, 11 pages, 2017.
Vargason et al., Comparison of Three Clinical Trial Treatments for Autism Spectrum Disorder Through Multivariate Analysis of Changes in Metabolic Profiles and Adaptive Behavior, Frontiers in Cellular Neuroscience, vol. 12, Article 503, 15 pages, 2018.
Vargason et al., Gastrointestinal Symptoms and Oral Antibiotic Use in Children with Autism Spectrum Disorder: Retrospective Analysis of a Privately Insured U.S. Population, Journal of Autism and Developmental Disorders 49:647-659, 13 pages, 2019.
Vuong et al., Emerging Roles for the Gut Microbiome in Autism Spectrum Disorder, Society of Biological Psychiatry, 13 pages, 2017.
Yang et al., Brain responses to biological motion predict treatment outcome in young children with autism, Translational Psychiatry, 8 pages, 2016.
Zwaigenbaum et al., Stability of Diagnostic Assessment for Autism Spectrum Disorder between 18 and 36 Months in a High-Risk Cohort, Autism Research 9:790-800, 11 pages, 2016.
Strijbis et al., Enzymology of the Carnitine Biosynthesis Pathway, IUBMB Life 62(5): 357-362, 6 pages, 2010.
Ming et al., Metabolic Perturbance in Autism Spectrum Disorders: A Metabolomics Study, Journal of Proteome Research, 7 pages, 2019.
Liu et al., Altered Urinary Amino Acids in Children With Autism Spectrum Disorders, Frontiers in Cellular Neuroscience, 9 pages, 2019.
International Search Report in related International Application No. PCT/US2020/026912, 19 pages, Jul. 31, 2020.
Extended European Search Report issued in related application EP20781937.6 on Apr. 20, 2023, 10 pages.
West et al., Metabolomics as a Tool for Discovery of Biomarkers of Autism Spectrum Disorder in the Blood Plasma of Children, PLOS One, vol. 9, Issue 11, Nov. 2014, 13 pages.
Dieme et al., Metabolomics Study of Urine in Autism Spectrum Disorders Using a Multiplatform Analytical Methodology, Journal of Proteome Research 2015, 14, 5273-5282, 2015, 10 pages.
Yap et al., Urinary Metabolic Phenotyping Differentiates Children with Autism from Their Unaffected Siblings and Age-Matched Controls, Journal of Proteome Research 2010, 9, 2996-3004, 2010, 9 pages.
Nadal-Desbarats, Combined 1H-NMR and 1H-13C HSQC-NMR to improve urinary screening in autism spectrum disorders, Analyst, 2014, 139, 3460, 2014, 10 pages.
Srikantha et al., Microbiota-gut-brain-axis and Autism Spectrum Disorders, doi:10.20944/preprints201811.0171.v1, 2018, 30 pages.
Canadian Intellectual Property Office, Office Action, Application No. 3,136,303, Mar. 20, 2025, 4 pages.
Wang, H. et al., "Potential serum biomarkers from a metabolomics study of autism", Journal of Psychiatry and Neuroscience, 41(1): 27-37, Sep. 22, 2015, pp. 27-37.
Canadian Intellectual Property Office, Office Action, Application No. 3,136,303, Mar. 20, 2026, 5 pages.

Classification Accuracy
Misclassification Error
Sample Index
ASD
TD
0
0.2
0.4
0.6
0.8
1
10
20
30
40
50
60

DIAGNOSTIC FOR CHILDHOOD RISK OF AUTISM SPECTRUM DISORDER

CROSS-REFERENCE TO RELATED APPLICATIONS

This application is a U.S. National Stage Application of International Application No. PCT/US2020/026912, filed Apr. 6, 2020, which claims priority from U.S. Provisional Patent Application No. 62/830,043, filed Apr. 5, 2019, the contents of all of which are incorporated herein by reference in their entirety.

FIELD

The present disclosure generally relates to specific and sensitive methods for early detection of autism spectrum disorder (ASD) in a child.

BACKGROUND

The diagnosis of autism spectrum disorder (ASD) is currently based on assessment of behavioral symptoms in patients considered to be at risk. Such symptoms include major impairments in social communication and skills, stereotyped motor behaviors, and tightly focused intellectual interests. Strong evidence exists that the underlying causes of ASD are present in earliest infancy and even prenatally, and involve a complex interaction of genetic and environmental factors. Yet, diagnosis of ASD at early ages is extremely difficult because some symptoms are simply not present in early infancy and other symptoms are difficult to distinguish from normal development. One national prevalence study of eight-year-olds with ASD found that the median age of diagnosis was 46 months for autism and 52 months for ASD; however, this study did not account for children and adults diagnosed at ages above eight years, so the true median age of diagnosis is even higher. Stable diagnoses of ASD have been found in children as young as 18 months, representing a significant disconnect between current and ideal outcomes.

At the same time, early diagnosis is important because available interventions are most effective if started early in life. A number of different intervention models have been demonstrated to be significantly helpful for many children with ASD, such as the Early Start Denver Model which has been found effective when started in early infancy. Early intervention may maximize the opportunity for improving neural connectivity while brain plasticity is still high, likely helping to reduce the severity of ASD or even prevent it from fully manifesting.

Even though ASD is currently diagnosed solely based upon clinical observations of children, certain physiological factors are believed to contribute or be affected by ASD. Development of a biomarker-based test for ASD, using quantifiable measures rather than qualitative judgement, could assist with screening for and diagnosing ASD earlier in childhood. This, in turn, would indicate if further evaluation is needed and allow for intervention and/or therapy to begin as early as possible. The value of ASD-related biomarkers goes beyond diagnosis, as they also offer the potential to evaluate treatment efficacy. This would serve as a complement to current behavioral and symptom assessments and help to further elucidate the underlying biological mechanisms affecting ASD symptoms. For example, multivariate statistical analysis of changes in plasma metabolites has been found to offer value for modeling changes in metabolic profiles and adaptive behavior resulting from clinical intervention. Functional neuroimaging biomarkers may also be promising indicators of biological response to treatment. In addition, eye-tracking metrics could represent further avenues for quantifying changes in behavior resulting from intervention and clinical trials. As with diagnostic biomarkers, such approaches can help to mitigate subjectivity in treatment assessment arising from the use of purely behavioral measures.

A need thus exists for efficient and reliable methods of early diagnosis of ASD in children, to indicate early intervention to prevent ASD and/or reduce the severity of symptoms.

SUMMARY OF THE INVENTION

One aspect of the present disclosure encompasses a method for diagnosing Autism Spectrum Disorder (ASD) in a subject suspected of having or at risk of having ASD. The method comprises measuring the level of one or a combination of two or more metabolites selected from the metabolites listed in Tables 1, 13, 14, and 17 in a biological sample obtained from the subject. A level of the one or combination of metabolites in the biological sample significantly different from the level of the one or combination of metabolites in a control panel of metabolite levels obtained from typically developing (TD) individuals is indicative of an ASD diagnosis.

The one or more metabolites can be measured by preparing a sample extract and using Ultrahigh Performance Liquid Chromatography-Tandem Mass Spectroscopy (UPLC-MS/MS) to obtain the levels of the one or the combination of two or more metabolites in the reconstituted sample extract. The sample extract can be prepared by subjecting the sample to methanol extraction, and a dried sample extract can be prepared from the methanol extraction. If a sample extract is dried, the dried sample extract is reconstituted for measuring the level of the one or combination of two or more metabolites. The method can further comprise removing protein from the biological sample.

A significantly different level of the one or combination of metabolites can be determined by applying each of the measured levels of the metabolites against a control panel of metabolite levels obtained from TD individuals. The control panel of metabolite levels can be stored on a computer system.

When the level of one metabolite is measured, applying each of the measured levels of the metabolite can comprise comparing the measured level of the metabolite in the sample to the level of the metabolite in the control panel of metabolite levels using a statistical analysis method selected from the standard Student t-test, the Welch test, the Mann-Whitney U test, the Welch t-test, and combinations thereof; and calculating the false discovery rate (FDR; calculates the p-value) and optionally the false positive rate (FPR; calculates the q-value) for the metabolite. A p-value of less than or about 0.05 and an FDR value of less than or about 0.1 can be indicative of an ASD diagnosis.

When the levels of a combination of two or more metabolites are measured, applying comprises calculating the Type I (FPR; false positive rate) and Type II (FNR; false negative rate) errors for the combination of metabolites using FDA or logistic regression. A Type I error of about or below 10% and a Type II error of about or below 10% can be indicative of an ASD diagnosis.

Another aspect of the present disclosure encompasses a method for diagnosing ASD in a subject suspected of having or at risk of having ASD. The method comprises obtaining or having obtained a biological sample from the subject; subjecting the sample to methanol extraction; drying the sample extract; reconstituting the sample extract; and measuring the level of one or a combination of two or more metabolites selected from the metabolites listed in Tables 1, 13, 14, and 17 in the reconstituted sample extract using Ultrahigh Performance Liquid Chromatography-Tandem Mass Spectroscopy (UHPLC-MS/MS). The method further comprises applying each of the measured levels of the metabolites against a control panel of metabolite levels obtained from typically developing (TD) individuals, wherein the panel is stored on a computer system. The method can further comprise removing protein from the biological sample.

When the level of one metabolite is measured, applying comprises comparing the measured level of the metabolite in the sample to the level of the metabolite in the control panel of metabolite levels using a statistical analysis method selected from the standard Student t-test, the Welch test, the Mann-Whitney U test, the Welch t-test, and combinations thereof; and calculating the false discovery rate (FDR; calculates the p-value) and optionally the false positive rate (FPR; calculates the q-value) for the metabolite. A p-value of less than or about 0.05 and an FDR value of less than or about 0.1 is indicative of an ASD diagnosis.

When the levels of a combination of two or more metabolites are measured, applying comprises calculating the Type I (FPR; false positive rate) and Type II (FNR; false negative rate) errors for the combination of metabolites using FDA or logistic regression. A Type I error of about or below 10% and a Type II error of about or below 10% is indicative of an ASD diagnosis.

Further, the level of a metabolite can be measured using Ultrahigh Performance Liquid Chromatography-Triple Quadrupole Mass Spectroscopy (UPLC-QQQ MS) with hydrophilic interaction chromatography (HILIC) chromatography.

The level of a metabolite can be calculated from a peak area and standard calibration curve obtained for the metabolite using the UPLC-MS/MS. Additionally, measuring metabolites can further include identifying each metabolite by automated comparison of the ion features in the sample extract to a reference library of chemical standard entries that included retention time, molecular weight (m/z), preferred adducts, and in-source fragments as well as associated MS spectra. The method can further comprise calculating the area under the curve (AUC) of the receiver operating characteristic (ROC) curve for each metabolite. When the levels of a combination of two or more metabolites are measured, a multivariate analysis can further be combined with leave-one-out cross-validation to analyze the success of the model on classification. In any of the aspects described above, the method can diagnose ASD at birth or pre-birth.

In any of the aspects described above, the biological sample can be urine. The level of one metabolite can be measured to diagnose ASD in the subject. The one metabolite can be selected from the metabolites listed in Table 1, Table 2, Table 7, and Table 17. In some aspects, the metabolite is 4-Hydroxy-3-methylbenzoic acid, N-Acetylethanolamine, 4-Pyridoxic acid, or Stearic acid.

The level of a combination of two metabolites can be measured to diagnose ASD in the subject. The two metabolites can be selected from the combination of metabolites listed in Table 3 and Table 8. In some aspects, the two metabolites are 4-Hydroxy-3-methylbenzoic acid and Tryptamine. In other aspects, the two metabolites are Gentisic acid and 4-Hydroxy-3-methylbenzoic acid.

The level of a combination of three metabolites can be measured to diagnose ASD in a subject. The three metabolites can be selected from the combination of metabolites listed in Table 4 and Table 9. In some aspects, the three metabolites are Acetylglucosamine, 4-Hydroxy-3-methylbenzoic acid, and Tryptamine. In other aspects, the three metabolites are Nicotinamide, Pipecolinic acid, and 4-Hydroxy-3-methylbenzoic acid.

The level of a combination of four metabolites can be measured to diagnose ASD in a subject. The four metabolites can be selected from the combination of metabolites in Table 5 and Table 10. In some aspects, the four metabolites are Tyrosine, Creatin, Nicotinamide, and 4-Hydroxy-3-methylbenzoic acid. In other aspects, the four metabolites are Amino valerate, N-Acetylneuraminic acid, Urocanic acid, and 4-Hydroxy-3-methylbenzoic acid.

The level of a combination of five metabolites can be measured. The five metabolites can be selected from the combination of metabolites in Table 6, Table 11, and Table 18. In some aspects, the five metabolites are Glycocyamine, Acetylglucosamine, 4-Hydroxy-3-methylbenzoic acid, Acetylornithine, and Tryptamine. In other aspects, the five metabolites are Anthranilic acid, N-Acetylethanolamine, Stearic acid, 4-Hydroxy-3-methylbenzoic acid, and Glyceric acid. In yet other aspects, the five metabolites are N-Acetylethanolamine, 4-Pyridoxic acid, Stearic acid, 4-Hydroxy-3-methylbenzoic acid, and 3-Aminoadipic acid. In other aspects, the five metabolites are Glycocyamine, 6-Hydroxynicotinic acid, 4-Hydroxy-3-methylbenzoic acid, Acetylornithine, and Tryptamine. In additional aspects, the five metabolites are Glycocyamine, Glutaconic acid, 6-Hydroxynicotinic acid, 4-Hydroxy-3-methylbenzoic acid, and Acetylornithine. In some aspects, the five metabolites are taurine, 4-Imidazoleacetic acid, xylose, phenylacetic acid, and uracil. In other aspects, the five metabolites are Taurine, Palmitic acid, 4-Imidazoleacetic acid, deoxythymidine monophosphate, and Shikimic acid. In yet other aspects, the five metabolites are Taurine, Imidazole, 4-Imidazoleacetic acid, deoxythymidine monophosphate, and Sebacic acid. In some aspects, the five metabolites are Taurine, 4-Imidazoleacetic acid, deoxythymidine monophosphate, Sebacic acid, and and 5-Hydroxytryptophan. Further, each metabolite can represent a group of metabolites correlated with the metabolite. In the methods, the levels of metabolites correlated with each metabolite can also be measured.

In some aspects, the biological sample is serum. When the biological sample is serum, the one or combination of two or more metabolites can be selected from the metabolites listed in Table 14. The levels of a combination of two metabolites can be measured, and the two metabolites can be 73.0@19.385714 and 105.0@22.546011. Alternatively, the levels of a combination of three metabolites can be measured, and the three metabolites can be 73.0@19.385714, 105.0@22.546011, and 208.0@27.66299. Further, the levels of a combination of four metabolites can be measured, and the four metabolites can be 73.0@19.385714, 105.0@22.546011, 208.0@27.66299, and 76.0@14.86401. The levels of a combination of five metabolites can also be measured, and the five metabolites can be 73.0@19.385714, 105.0@22.546011, 208.0@27.66299, 76.0@14.86401, and 207.0@22.571007.

In some aspects, the biological sample is whole blood. In one alternative of the aspects, the levels of a combination of two metabolites are measured, and the two metabolites are 6-Hydroxynicotinic acid and 2-Aminoadipic acid. In other aspects, the levels of a combination of three metabolites are measured, and the three metabolites are 2,3-Dihydroxybenzoic acid, Cadaverine, and Galactonic acid. In other aspects, the levels of a combination of four metabolites are measured, and the four metabolites are 2,3-Dihydroxybenzoic acid, 6-Hydroxynicotinic acid, 2-Aminoadipic acid, and 13C5-15N-Glutamic acid. In yet other aspects, the levels of a combination of five metabolites are measured, and the five metabolites are 2,3-Dihydroxybenzoic acid, 2-Aminoadipic acid, 13C5-15N-Glutamic acid, Methylmalonic acid, and Levulinic acid.

The method can diagnose ASD with a sensitivity of at least about 70% to 95% or more, a specificity of at least about 70% to 95% or more, or both. The method can also diagnose ASD with a misclassification error of about 10% to about 20%.

The method can further comprise assigning a medical, behavioral, and/or nutritional treatment protocol to a subject suspected of having or at risk of having ASD. A treatment protocol can be personalized to the subject. For instance, a treatment protocol can be personalized based on the metabolites found to be significantly different in a sample obtained from the subject when compared to a control and identified using the method described herein. Such a personalized treatment protocol can include adjusting in the subject the level of the one or a combination of two or more metabolites found to be significantly different in a sample obtained from the subject. The treatment protocol can also include adjusting the levels of one or more metabolites associated with the one or combination of two or more metabolites identified as having a level in the biological sample significantly different from the level of the one or combination of metabolites in the control sample.

Yet another aspect of the present disclosure encompasses a method of determining a personalized treatment protocol for a subject suspected of having or at risk of having ASD. The method comprises measuring in a biological sample obtained from the subject the level of one or combination of two or more metabolites selected from the metabolites listed in Tables 1, 13, 14, and 17 and any combination thereof, identifying one or a combination of metabolites having a level in the biological sample significantly different from the level of the one or combination of metabolites in a control sample, and assigning a personalized medical, behavioral, or nutritional treatment protocol to the subject.

Another aspect of the present disclosure encompasses a method of monitoring the therapeutic effect of an ASD treatment protocol in a subject suspected of having or at risk of having ASD. The method comprises measuring in a first biological sample obtained from the subject the level of one or a combination of metabolites selected from the metabolites listed in Tables 1, 13, 14, and 17 and any combination thereof, measuring in a second biological sample obtained from the subject the level of the one or combination of metabolites, and comparing the levels of the one or combination of metabolites in the first sample and the second sample, wherein maintenance of the level of the one or combination of metabolites or a change of the level of the one or combination of metabolites to a level of the one or combination of metabolites in a control sample is indicative that the treatment protocol is therapeutically effective in the subject.

One aspect of the present disclosure encompasses a kit for performing any of the methods described above. The kit comprises (a) a container for collecting the biological sample from the subject; (b) solutions and solvents for preparing an extract from a biological sample obtained from the subject; and (c) instructions for (i) preparing the extract, (ii) measuring the level of one or more metabolites selected from the metabolites listed in Tables 1, 13, 14, and 17 using Ultrahigh Performance Liquid Chromatography-Tandem Mass Spectroscopy (UPLC-MS/MS); and (iii) applying the measured metabolite levels against a control panel of metabolite levels obtained from typically developing (TD) individuals.

DETAILED DESCRIPTION

Figure 1:
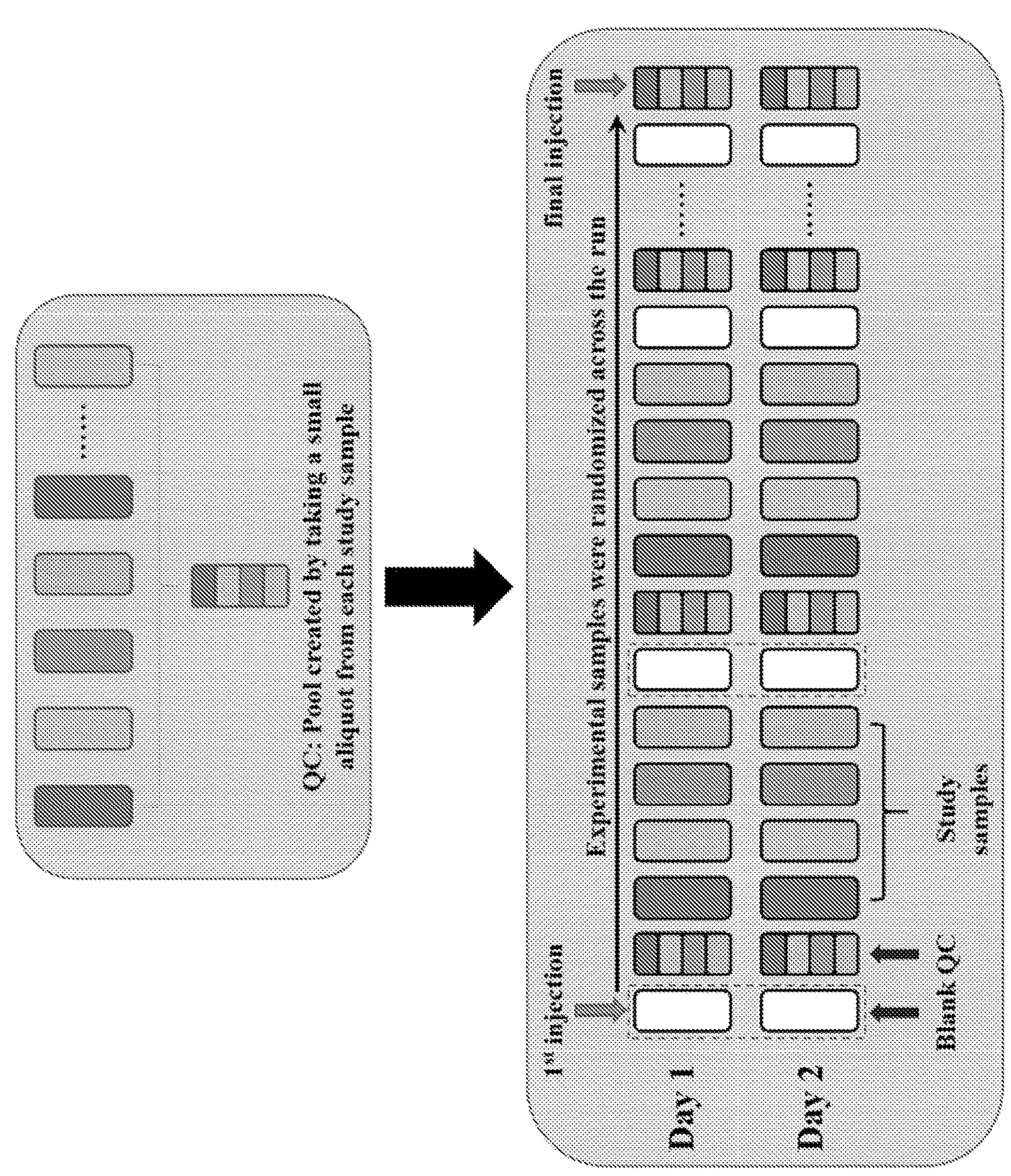
FIG. 1. Preparation of QC and Blank samples. A small aliquot of each study sample (colored cylinders) is pooled to create a QC technical replicate sample (multi-colored cylinder), which is then injected periodically throughout the platform run. Variability of metabolites in this QC sample can be used to calculate an estimate of overall process and platform variability.

The present disclosure is based in part on the surprising discovery of metabolite biomarkers measured in a biological sample obtained from a subject and methods of using the biomarkers to diagnose ASD, with a high level of sensitivity and specificity. Surprisingly, the biomarkers can be detected in a urine sample, an easily obtainable sample when compared to, e.g., blood or plasma. The biomarkers can be used to diagnose ASD shortly after a child is born.

I. Methods

One aspect of the present disclosure provides a method of diagnosing ASD. The method comprises measuring the level of metabolites in a biological sample obtained from the subject.

The subject can be, without limitation, a human, a non-human primate, a mouse, a rat, a guinea pig, or a dog. In some aspects, the subject is a human subject. The subject can be a premature newborn, a term newborn, a neonate, an infant, a toddler, a young child, a child, an adolescent, a pediatric patient, or a geriatric patient. In one aspect, the subject is a child patient below about 18, 15, 12, 10, 8, 6, 4, 3, 2, or 1 year old. In another aspect, the subject is an adult patient. In another aspect, the subject is an elderly patient. In another aspect, the subject is between 1 and 5, between 2 and 10, between 3 and 18, between 21 and 30, between 21 and 40, between 21 and 50, between 50 and 90, between 60 and 90, between 70 and 90, between 60 and 80, or between 65 and 75 years old.

A sample may include, but is not limited to, a cell, a cellular organelle, an organ, a tissue, a tissue extract, a biofluid, or an entire organism. The sample may be a heterogeneous or homogeneous population of cells or tissues. As such, metabolite levels or concentrations can be measured within cells, tissues, organs, or other biological samples obtained from the subject. For instance, the biological sample can be bone marrow extract, whole blood, blood plasma, serum, peripheral blood, urine, phlegm, synovial fluid, milk, saliva, mucus, sputum, exudates, cerebrospinal fluid, intestinal fluid, cell suspensions, tissue digests, tumor cell containing cell suspensions, cell suspensions, and cell culture fluid which may or may not contain additional substances (e.g., anticoagulants to prevent clotting). The sample can comprise cells or can be cell-free. In some aspects, the sample is a urine sample. In other aspects, the sample is a whole blood sample. In some aspects, the sample is a serum sample.

In some aspects, multiple biological samples may be obtained for diagnosis by the methods of the present invention, e.g., at the same or different times. A sample or samples obtained at the same or different times can be stored and/or analyzed by different methods.

Methods for obtaining and extracting the metabolome from a wide range of biological samples, including cell cultures, urine, blood/serum, and both animal- and plant-derived tissues are known in the art. Although these protocols are readily available, the variable stability of metabolites and the source of a sample means that even minor changes in procedure can have a major impact on the observed metabolome. For instance, the fast turnover rate of enzymes and the variable temperature and chemical stability of metabolites require that metabolomics samples be collected quickly and handled uniformly, and that all enzymatic activity be rapidly quenched in order to minimize biologically irrelevant deviations between samples that may result from the processing protocol.

A metabolomics extraction protocol can focus on a subset of metabolites (for example, water-soluble metabolites or lipids). Furthermore, an extraction protocol may focus on either a highly reproducible and quantitative extraction of a restricted set of metabolites (that is, targeted metabolomics) or the global collection of all possible metabolites (that is, untargeted metabolomics). In some aspects, a metabolomics extraction protocol focuses on extraction of short chain fatty acids (SOFA). In one alternative of the aspects, a metabolomics extraction protocol focuses on extraction of short chain fatty acids (SOFA) from serum samples. In other aspects, a metabolomics extraction protocol is targeted. In yet other aspects, a metabolomics extraction protocol is untargeted.

In some aspects, sample extracts are prepared by subjecting the sample to methanol extraction to remove proteins, dissociate small molecules bound to protein or trapped in the precipitated protein matrix, and to recover chemically diverse metabolites. In one aspect, a dried sample extract is prepared from the methanol extraction. A dried sample can then be reconstituted in a solvent for measuring the level of the one or combination of two or more metabolites.

Methods of measuring the level of metabolites in a sample are known in the art. The methods can and will vary depending on the metabolites, the number of metabolites to be measured, and the biological sample in which the metabolites are measured, among other variables, and can be determined experimentally. Such concentration can be expressed in many ways including, for example, the number of molecules per unit weight or unit volume, and the relative ratio between the levels of two metabolites, wherein optionally, one of the two metabolites is a control metabolite that substantially maintains its levels regardless of any treatment. Metabolite abundance or levels may be identified using, for example, Mass Spectrometry such as MALDI/TOF (time-of-flight), SELDI/TQF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, Ultrahigh Performance Liquid Chromatography-Tandem Mass Spectroscopy (UPLC-MS/MS), tandem mass spectrometry (e.g., MS/MS, MS/MS/MS, ESI-MS MS etc.), secondary ion mass spectrometry (SIMS), and/or ion mobility spectrometry (e.g. GC-FMS, FMS-MS, LC-FMS, LC-FMS-MS among others), enzyme assays, and variations on these methods.

In some aspects, a sample extract is subjected to one or more than one measurement. For instance, a sample can be divided into more than one aliquot to measure metabolites using more than one analytical method. In some aspects, the level of metabolites in aliquots of the sample extract is measured using Ultrahigh Performance Liquid Chromatography-Triple Quadrupole Mass Spectroscopy (UPLC-QQQ MS) with hydrophilic interaction chromatography (HILIC) chromatography.

The level of a metabolite can be determined from a peak area and standard calibration curve obtained for the metabolite using the UPLC-MS/MS. Additionally, measuring metabolites can further include identifying each metabolite such as by automated comparison of the ion features in the sample extract to a reference library of chemical standard entries that include retention time, molecular weight (m/z), preferred adducts, and in-source fragments as well as associated MS spectra.

The method comprises measuring the level of one or a combination of two or more metabolites in the sample. For instance, the level of one or the levels of 2, 3, 4, 5, 6, 7, 8, 9, 10, 15, 20, 25, 30, 40, 50, 60 or more metabolites can be measured. The metabolites and combinations of metabolites can be selected from the metabolites listed in Tables 1, 13, 14, and 17.

A level of the measured one or combination of metabolites in the biological sample significantly different from the level of the one or combination of metabolites in a control panel of metabolite levels is indicative of an ASD diagnosis. A significantly different level of the one or combination of metabolites can be determined by applying each of the measured levels of the metabolites against a control panel of metabolite levels created by measuring metabolite levels of the one or combination of metabolites in control TD subjects. The panel can be stored on a computer system. It is noted that a significant difference in the level of the metabolite can be an increase or a decrease in the level of the metabolite in the sample when compared to the level of the metabolite in the control panel of metabolite levels. The method can also further comprise calculating the area under the curve (AUC) of the receiver operating characteristic (ROC) curve for each metabolite. When the levels of a combination of two or more metabolites are measured, a multivariate analysis can further be combined with leave-one-out cross-validation to analyze the success of the model on classification.

In some aspects, the level of one metabolite is measured. When the level of one metabolite is measured, applying each of the measured levels of the metabolites can comprise comparing the measured level of the metabolite in the sample to the level of the metabolite in the control panel of metabolite levels using a statistical analysis method. Non-limiting examples of statistical analysis methods suitable for use when one metabolite is measured include analysis of variance (ANOVA), chi-squared test, correlation, factor analysis, Mann-Whitney U, Mean square weighted deviation (MSWD), Pearson product-moment correlation coefficient, regression analysis, Spearman's rank correlation coefficient, Student's t-test, Time series analysis, and Conjoint Analysis, among others, and combinations thereof. In some aspects, when the level of one metabolite is measured, applying each of the measured levels of the metabolites can comprise comparing the measured level of the metabolite in the sample to the level of the metabolite in the control panel of metabolite levels using a statistical analysis method selected from the standard Student t-test, the Welch test, the Mann-Whitney U test, the Welch t-test, and combinations thereof; and calculating the false discovery rate (FDR; calculates the p-value) and optionally the false positive rate (FPR; calculates the q-value) for the metabolite. In some aspects, a p-value of less than or about 0.05 and an FDR value of less than or about 0.1 is indicative of an ASD diagnosis.

When the level of one metabolite is measured to diagnose ASD in a urine sample, the one metabolite can be selected from the metabolites listed in Table 1, Table 2, Table 7, and Table 17. In some aspects, the metabolite is selected from 4-Hydroxy-3-methylbenzoic acid, N-Acetylethanolamine, 4-Pyridoxic acid, or Stearic acid.

When the level of one metabolite is measured to diagnose ASD in a serum sample, the one metabolite can be selected from the metabolites listed in Table 14. In some aspects, the serum metabolites are SOFA metabolites.

When the levels of a combination of two or more metabolites are measured, applying each of the measured levels of the metabolites against a control panel of metabolite levels obtained from typically developing (TD) individuals comprises calculating the Type I (FPR; false positive rate) and Type II (FNR; false negative rate) errors for the combination of metabolites using FDA or logistic regression. A Type I error of about or below 30, 25, 20, 15, or 10% and a Type II error of about or below 30, 25, 20, 15, or 10% is indicative of an ASD diagnosis.

In some aspects, the level of a combination of two metabolites is measured to diagnose ASD. When the metabolites are measured in urine samples, the two metabolites can be selected from the combination of metabolites listed in Table 3 and Table 8. In some aspects, the two metabolites are 4-Hydroxy-3-methylbenzoic acid and Tryptamine. In other aspects, the two metabolites are 4-Hydroxy-3-methylbenzoic acid and Tryptamine. In other aspects, the two metabolites are Gentisic acid and 4-Hydroxy-3-methylbenzoic acid.

When the metabolites are measured in serum samples, the two metabolites can be 73.0@19.385714 and 105.0@22.546011. When the metabolites are measured in whole blood samples, the two metabolites can be 6-Hydroxynicotinic acid and 2-Aminoadipic acid.

The level of a combination of three metabolites can be measured to diagnose ASD. When the metabolites are measured in urine samples, the three metabolites can be selected from the combination of metabolites listed in Table 4 and Table 9. In some aspects, the three metabolites are Acetylglucosamine, 4-Hydroxy-3-methylbenzoic acid, and Tryptamine. In other aspects, the three metabolites are Nicotinamide, Pipecolinic acid, and 4-Hydroxy-3-methylbenzoic acid.

When the level of three metabolites is measured in serum samples, the three metabolites can be 73.0@19.385714, 105.0@22.546011, and 208.0@27.66299. When the level of three metabolites is measured in whole blood samples, the three metabolites can be 2,3-Dihydroxybenzoic acid, Cadaverine, and Galactonic acid.

The level of a combination of four metabolites can be measured to diagnose ASD. When the metabolites are measured in urine samples, the four metabolites can be selected from the combination of metabolites in Table 5 and Table 10. In some aspects, the four metabolites are Tyrosine, Creatin, Nicotinamide, and 4-Hydroxy-3-methylbenzoic acid. In other aspects, the four metabolites are Amino valerate, N-Acetylneuraminic acid, Urocanic acid, and 4-Hydroxy-3-methylbenzoic acid.

When the level of four metabolites is measured in serum samples, the four metabolites can be 73.0@19.385714, 105.0@22.546011, 208.0@27.66299, and 76.0@14.86401. When the level of four metabolites is measured in whole blood samples, the four metabolites can be 2,3-Dihydroxybenzoic acid, 6-Hydroxynicotinic acid, 2-Aminoadipic acid, and 13C5-15N-Glutamic acid.

The level of a combination of five metabolites can be measured. When the metabolites are measured in urine samples, the five metabolites can be selected from the combination of metabolites in Table 6 and Table 11. In some aspects, the five metabolites are Glycocyamine, Acetylglucosamine, 4-Hydroxy-3-methylbenzoic acid, Acetylornithine, and Tryptamine. In other aspects, the five metabolites are Anthranilic acid, N-Acetylethanolamine, Stearic acid, 4-Hydroxy-3-methylbenzoic acid, and Glyceric acid. In yet other aspects, the five metabolites are N-Acetylethanolamine, 4-Pyridoxic acid, Stearic acid, 4-Hydroxy-3-methylbenzoic acid, and 3-Aminoadipic acid. In other aspects, the five metabolites are Glycocyamine, 6-Hydroxynicotinic acid, 4-Hydroxy-3-methylbenzoic acid, Acetylornithine, and Tryptamine. In additional aspects, the five metabolites are Glycocyamine, Glutaconic acid, 6-Hydroxynicotinic acid, 4-Hydroxy-3-methylbenzoic acid, and Acetylornithine. In yet other aspects, the five metabolites are taurine, 4-Imidazoleacetic acid, xylose, phenylacetic acid, and uracil. In some aspects, the five metabolites are Taurine, Palmitic acid, 4-Imidazoleacetic acid, deoxythymidine monophosphate, and Shikimic acid. In other aspects, the five metabolites are Taurine, Imidazole, 4-Imidazoleacetic acid, deoxythymidine monophosphate, and Sebacic acid. In additional aspects, the five metabolites are Taurine, 4-Imidazoleacetic acid, deoxythymidine monophosphate, Sebacic acid, and 5-Hydroxytryptophan.

When the level of five metabolites is measured in serum samples, the five metabolites can be 73.0@19.385714, 105.0@22.546011, 208.0@27.66299, 76.0@14.86401, and 207.0@22.571007. When the level of five metabolites is measured in whole blood samples, the five metabolites can be 2,3-Dihydroxybenzoic acid, 2-Aminoadipic acid, 13C5-15N-Glutamic acid, Methylmalonic acid, and Levulinic acid.

Further, more than one combination of metabolites can be used to further improve the accuracy of an ASD diagnosis, including improving specificity and sensitivity, and reducing misclassification errors. For instance, the diagnosis obtained from a measurement of a combination of two metabolites in a urine sample can be combined with results from a combination of three SOFA metabolites measured in a serum sample to improve accuracy of a diagnosis.

Further, each metabolite can represent a group of metabolites correlated with the metabolite. In the methods, the levels of metabolites correlated with each metabolite can also be measured.

The method can diagnose ASD with a high level of sensitivity. For instance, the method can diagnose ASD with a sensitivity greater than or equal to 70%, greater than or equal to 81%, greater than or equal to 90%, greater than or equal to 95%, greater than or equal to 98%, or greater than or equal to 99%. The method can also diagnose ASD with a high level of specificity. For instance, the method can diagnose ASD with a specificity greater than or equal to 70%, greater than or equal to 81%, greater than or equal to 90%, greater than or equal to 95%, or greater than or equal to 98%, or greater than or equal to 99%. In some aspects, the method can diagnose ASD with a sensitivity of at least about 80% to 90%, a specificity of at least about 80% to 90%, or both.

The method can also diagnose ASD with a low misclassification error, such as a misclassification error of about 40, 35, 30, 25, 20, 15, 10, 5, 1% or lower, or about 25, 24, 23, 22, 21, 20, 19, 18, 17, 16, 15, 14, 13, 12, 11, or about 10%. In some aspects, the method can diagnose ASD with a misclassification error of about 13% to about 17% or less.

The method can further comprise assigning a medical, behavioral, and/or nutritional treatment protocol to the subject when the subject is diagnosed with ASD. Non-limiting examples of treatment protocols include behavioral management therapy, cognitive behavior therapy, early intervention, educational and school-based therapies, joint attention therapy, medication treatment, nutritional therapy, occupational therapy, parent-mediated therapy, physical therapy, social skills training, speech-language therapy, and combinations thereof. Non-limiting examples of medication treatment include antipsychotic drugs, such as risperidone and aripripazole, for treating irritability associated with ASD, selective serotonin re-uptake inhibitors (SSRIs), tricyclics, psychoactive or anti-psychotic medications, stimulants, anti-anxiety medications, anticonvulsants, nutritional supplementation, and Microbiota Transfer Therapy (MTT).

In one aspect, the treatment protocol is supplementation with the metabolite. The metabolite can be supplemented by nutritional means, or by oral or parenteral administration of compositions comprising the metabolite. In one aspect, the treatment protocol is MTT. MTT comprises transfer of purified gut bacteria from a healthy person to the subject. Methods of performing MTT are known in the art and can be as described in, e.g., Kang, et al., "Microbiota Transfer Therapy alters gut ecosystem and improves gastrointestinal and autism symptoms: An open-label study," Microbiome 2017, 5, 10.

Treatment protocols can comprise restoring the level of one or more metabolites identified as significantly different in the biological sample obtained from the subject to a level of the one or more metabolites in the control panel of metabolite levels obtained from TD individuals. Similarly, when a metabolite represents a group of metabolites correlated with the metabolite, the treatment protocol can comprise restoring the level of one or more of the group of metabolites associated with the identified metabolite. The level of a metabolite can be restored by about 20%, 30%, 40%, 50%, 60%, 70%, 80%, 90% or more.

A treatment protocol can be personalized to the subject. For instance, a treatment protocol can be personalized based on the metabolites found to be significantly different in a sample obtained from the subject when compared to a control and identified using the method described herein. Such a personalized treatment protocol can include adjusting in the subject the level of the one or combination of metabolites. The treatment protocol can also include adjusting the levels of one or more metabolites associated with the one or combination of two or more metabolites identified as having a level in the biological sample significantly different from the level of the one or combination of metabolites in the control sample.

Another aspect of the present disclosure encompasses a method for diagnosing ASD in a subject suspected of having or at risk of having ASD. The method comprises obtaining or having obtained a biological sample from the subject; subjecting the sample to methanol extraction; drying the sample extract; reconstituting the sample extract; and measuring the level of one or a combination of two or more metabolites selected from the metabolites listed in Tables 1, 13, 14, and 17 in the reconstituted sample extract using Ultrahigh Performance Liquid Chromatography-Tandem Mass Spectroscopy (UHPLC-MS/MS). The method further comprises applying each of the measured levels of the metabolites against a control panel of metabolite levels obtained from typically developing (TD) individuals, wherein the panel is stored on a computer system. The method can further comprise removing protein from the biological sample.

When the level of one metabolite is measured, applying comprises comparing the measured level of the metabolite in the sample to the level of the metabolite in the control panel of metabolite levels using a statistical analysis method selected from the standard Student t-test, the Welch test, the Mann-Whitney U test, the Welch t-test, and combinations thereof; and calculating the false discovery rates (FDR; calculates the p-value) and optionally the false positive rate (FPR; calculates the q-value) for the metabolite. A p-value of less than or about 0.05 and an FDR value of less than or about 0.1 is indicative of an ASD diagnosis.

When the levels of a combination of two or more metabolites are measured, applying comprises calculating the Type I (FPR; false positive rate) and Type II (FNR; false negative rate) errors for the combination of metabolites using FDA or logistic regression. A Type I error of about or below 10% and a Type II error of about or below 10% is indicative of a risk of an ASD diagnosis.

Yet another aspect of the present disclosure encompasses a method of determining a personalized treatment protocol for a subject having or at risk of having ASD. The method comprises measuring in a biological sample obtained from the subject the level of one or combination of two or more metabolites selected from the metabolites listed in Tables 1, 13, 14, and 17 and any combination thereof, identifying one or a combination of metabolites having a level in the biological sample significantly different from the level of the one or combination of metabolites in a control sample, and assigning a personalized medical, behavioral, or nutritional treatment protocol to the subject.

Another aspect of the present disclosure encompasses a method of monitoring the therapeutic effect of an ASD treatment protocol in a subject having or at risk of having ASD. The method comprises measuring in a first biological sample obtained from the subject the level of one or a combination of metabolites selected from the metabolites listed in Tables 1, 13, 14, and 17 and any combination thereof, measuring in a second biological sample obtained from the subject the level of the one or combination of metabolites, and comparing the level of the one or combination of metabolites in the first sample and the second sample, wherein maintenance of the level of the one or combination of metabolites or a change of the level of the one or combination of metabolites to a level of the one or combination of metabolites in a control sample is indicative that the treatment protocol is therapeutically effective in the subject.

The methods provided herein result in, or are aimed at achieving a detectable improvement in one or more indicators or symptoms of ASD in a subject suspected of having or at risk of having ASD. The one or more indicators or symptoms of ASD include, without limitation, changes in eye tracking, skin conductance, and/or EEG measurements in response to visual stimuli, difficulties engaging in and responding to social interaction, verbal and nonverbal communication problems, repetitive behaviors, intellectual disability, difficulties in motor coordination, attention issues, sleep disturbances, and physical health issues such as gastrointestinal disturbances.

Several screening instruments are known in the art for evaluating a subject's social and communicative development and thus can be used as aids in screening for and detecting changes in the severity of impairment in communication skills, social interactions, and restricted, repetitive, and stereotyped patterns of behavior characteristic of autism spectrum disorder. Evaluation can include neurologic and genetic assessment, along with in-depth cognitive and language testing. Additional measures developed specifically for diagnosing and assessing autism include the Autism Diagnosis Interview-Revised (ADI-R), the Autism Diagnostic Observation Schedule (ADOS-G), and the Childhood Autism Rating Scale (CARS).

According to CARS, evaluators rate the subject on a scale from 1 to 4 in each of 15 areas: Relating to People; Imitation; Emotional Response; Body Use; Object Use; Adaptation to Change; Visual Response; Listening Response; Taste, Smell, and Touch Response and Use; Fear; Verbal Communication; Nonverbal Communication; Activity; Level and Consistency of Intellectual Response; and General Impressions. A second edition of CARS, known as the Childhood Autism Rating Scale-2 or CARS-2, was developed by Schopler et al. (Childhood Autism Rating Scale Second edition (CARS2): Manual. The original CARS was developed primarily with individuals with co-morbid intellectual functioning and was criticized for not accurately identifying higher functioning individuals with ASD. CARS-2 retained the original CARS form for use with younger or lower functioning individuals (now renamed the CARS2-ST for "Standard Form"), but also includes a separate rating scale for use with higher functioning individuals (named the CARS2-HF for "High Functioning") and an unscored information-gathering scale ("Questionnaire for Parents or Caregivers" or CARS2-QPC) that has utility for making CARS2ST and CARS2-HF ratings.

Another symptom-rating instrument useful for assessing changes in symptom severity before, during, or following treatment according to a method provided herein is the Aberrant Behavior Checklist (ABC). The ABC is a symptom rating checklist used to assess and classify problem behaviors of children and adults in a variety of settings. The ABC includes 58 items that resolve onto five subscales: (1) irritability/agitation, (2) lethargy/social withdrawal, (3) stereotypic behavior, (4) hyperactivity/noncompliance, and (5) inappropriate speech.

II. Kits

One aspect of the present disclosure encompasses a kit for performing any of the methods described above. The kit comprises (a) a container for collecting the biological sample from the subject; (b) solutions and solvents for preparing an extract from a biological sample obtained from the subject; and (c) instructions for (i) preparing the extract, (ii) measuring the level of one or more metabolites selected from the metabolites listed in Table 1 using Ultrahigh Performance Liquid Chromatography-Tandem Mass Spectroscopy (UPLC-MS/MS); and (iii) applying the measured metabolite levels against a control panel of metabolite levels obtained from typically developing (TD) individuals.

As used herein, "kits" refer to a collection of elements including at least one non-standard laboratory reagent for use in the disclosed methods, in appropriate packaging, optionally containing instructions for use. A kit may further include any other components required to practice the methods, such as dry powders, concentrated solutions, or ready-to-use solutions. In some aspects, a kit comprises one or more containers that contain reagents for use in the methods. Containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

A kit may include instructions for testing a biological sample of a subject suspected of having or at risk of having ASD. The instructions will generally include information about the use of the kit in the disclosed methods. In other aspects, the instructions may include at least one of the following: description of possible therapies including therapeutic agents; clinical studies; and/or references. The instructions may be printed directly on the container (when present), or as a label applied to the container, or as a separate sheet, pamphlet, card, or folder supplied in or with the container.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the administration of an agent or drug to a subject or patient includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures. In the context of autism spectrum disorder, "treat" and "treating" encompass alleviating, ameliorating, delaying the onset of, inhibiting the progression of, or reducing the severity of one or more symptoms associated with an autism spectrum disorder.

As used herein, "therapeutically effective amount" or "pharmaceutically active dose" refers to an amount of a composition which is effective in treating the named disease, disorder or condition.

The terms "sensitivity" and "specificity" are statistical measures of the performance of a binary classification test. Sensitivity (also called the true positive rate, the recall, or probability of detection in some fields) measures the proportion of actual positives that are correctly identified as such (e.g., the percentage of sick people who are correctly identified as having the condition). Specificity (also called the true negative rate) measures the proportion of actual negatives that are correctly identified as such (e.g., the percentage of healthy people who are correctly identified as not having the condition). The terms "positive" and "negative" do not refer to the value of the condition of interest, but to its presence or absence. The condition itself could be a disease, so that "positive" might mean "diseased", while "negative" might mean "healthy". In many tests, including diagnostic medical tests, sensitivity is the extent to which actual positives are not overlooked (so false negatives are few), and specificity is the extent to which actual negatives are classified as such (so false positives are few). As such, a highly sensitive test rarely overlooks an actual positive (for example, overlooking a disease condition); a highly specific test rarely registers a positive classification for anything that is not the target of testing (for example, diagnosing a disease condition in a healthy subject); and a test that is highly sensitive and highly specific does both.

A metabolite is a small molecule intermediate or end product of metabolism. Metabolites have various functions, including fuel, structure, signalling, stimulatory and inhibitory effects on enzymes, catalytic activity of their own (usually as a cofactor to an enzyme), defense, and interactions with other organisms (e.g. pigments, odorants, and pheromones). A primary metabolite is directly involved in normal "growth", development, and reproduction.

The metabolome refers to the complete set of small-molecule chemicals found within a biological sample. The biological sample can be a cell, a cellular organelle, an organ, a tissue, a tissue extract, a biofluid or an entire organism. The small molecule chemicals found in a given metabolome may include both endogenous metabolites that are naturally produced by an organism (such as amino acids, organic acids, nucleic acids, fatty acids, amines, sugars, vitamins, co-factors, pigments, antibiotics, etc.) as well as exogenous chemicals (such as drugs, environmental contaminants, food additives, toxins and other xenobiotics) that are not naturally produced by an organism.

As various changes could be made in the above-described metabolites and methods without departing from the scope of the invention, it is intended that all matter contained in the above description and in the examples given below shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: Identification and Characterization of Urine Metabolites Associated with ASD Urine samples were collected from 23 young children with ASD. Control urine samples were also collected from 28 young typically developing (TD) children. The levels of 26 metabolites measured in the whole blood samples were significantly different ($q<0.1$) in the samples from young children with ASD when compared to the samples from the typically developing (TD) young children, after using False Discovery Methods to eliminate false positives. All combinations of 2, 3, 4, and 5 of those metabolites were analyzed to identify the combinations with the highest sensitivity and specificity. Many combinations had positive results. The most significant results were:

- Combination of 2 metabolites: 4-Hydroxy-3-methylbenzoic acid; Tryptamine; sensitivity 80.769%; specificity 82.609%.
- Combination of 3 metabolites: Acetylglucosamine; 4-Hydroxy-3-methylbenzoic acid; Tryptamine; sensitivity 82.609%, specificity 84.615%.
- Combination of 4 Metabolites: Tyrosine; Creatine; Nicotinamide; 4-Hydroxy-3-methyl benzoic acid; sensitivity 82.609%, specificity 84.615%
- Combination of 5 Metabolites: Glycocyamine; Acetylglucosamine; 4-Hydroxy-3-methylbenzoic acid; Acetylornithine; Tryptamine; sensitivity 86.597%, specificity 88.462%

Other combinations of metabolites selected from the 185 metabolites also had positive results. Some of the more significant positive results included:

- Combination of 2 metabolites: Gentisic acid; 4-Hydroxy-3-methylbenzoic acid; sensitivity 78.261%, specificity 76.923%
- Combination of 3 metabolites: Nicotinamide; Pipecolinic acid; 4-Hydroxy-3-methylbenzoic acid; sensitivity 86.957%, specificity 84.615%
- Combination of 4 metabolites: Amino valerate; N-Acetylneuraminic acid; Urocanic acid; 4-Hydroxy-3-methylbenzoic acid; sensitivity 91.304%, specificity 88.462%
- Combination of 5 metabolites: Anthranilic acid; N-Acetylethanolamine; Stearic acid; 4-Hydroxy-3-methylbenzoic acid; Glyceric acid; sensitivity 95.652%, specificity 92.308%

More detailed results are included in Examples 2-4 below. Methods used are as detailed in Examples 5 and 6.

Leave-one-out cross-validation was used to determine the best combination to ensure that the results are not just fitted well, but that they are statistically independent. In short, cross-validation leaves out a sample, then determines the best combination of the remaining samples, and finally tests this best combination on the sample that was left out. After this the sample is put back into the dataset and a different sample is removed, whereupon the entire procedure is repeated. This process continues until each sample has been left out one time. This cross-validation procedure ensures that we choose the best combination not just from fitting the results but from predicting results for the samples which were left out.

Larger sample sizes are required to validate the results, and may result in slightly different combinations of the metabolites being the most significant. The bottom line is that a small set of 2-5 metabolites can be used to differentiate between young children with ASD and young TD children, with a high sensitivity and specificity.

These results are novel because currently there is no approved medical diagnostic for ASD. It is highly likely that these results will apply to younger children, possibly with a somewhat different combination and reference range being best for different ages. These metabolites may also be useful to monitor the effectiveness of treatment interventions.

Example 2: Search for the Most Significant Individual Metabolites

First univariate analysis was performed using hypothesis testing to test for differences between the population mean/median of each group of children. First, the metabolite measurements were tested for normality using the Anderson-Darling test. If both groups accepted the null hypothesis of that test, the F-test was used to determine if the population variances for each group were equal. This resulted in either the Student's t-test (for equal) or the Welch's test (for unequal) being used to test for significant differences in the population means. If at least one of the groups rejected the null hypothesis of the Anderson-Darling test, the two-sample Kolmogorov-Smirnov test was used to determine if the measurements from both groups came from distributions of the same shape. If the samples accepted the null hypothesis of the Kolmogorov-Smirnov test, the Mann-Whitney U test was used to test for significant differences between the medians of the two samples. If the samples rejected the null hypothesis of the Kolmogorov-Smirnov test, the measurements were shifted over by the mean of the samples and the Kolmogorov-Smirnov test was performed again. If the samples accepted the null hypothesis, the Mann-Whitney U test would be used to test for significant differences between the population medians. If the samples still rejected the null hypothesis, the Welch's test would be used to test for significant differences in the population mean. Each test was done with a significance of 5%.

Then, False Discovery Rate (FDR) methods were used to correct for multiple-hypothesis testing. This resulted in a set of 26 metabolites that had $p<0.05$ (from hypothesis testing) and $FDR<0.1$. See Table 1.

TABLE 1

Most significant metabolites.

| Measurements | Pathway | Test | p-Value | FDR | ASD/NT Mean |
|---|---|---|---|---|---|
| Acetylcarnitine | fatty acid metabolism | mannW | 0.001717 | 0 | 0.493285941 |
| Kynurenic acid | 'Lipids/phospholipids, ligand' | mannW | 0.0218 | 0 | 0.791949724 |
| 4-lmidazoleacetic acid | 'Phenylalanine metabolism/ Tyrosine metabolism/Phenyl alanine metabolism' | mannW | 0.014931 | 0 | 0.628779883 |
| Tyrosine | 'Cholesterol metabolism/fatty acids' | mannW | 0.001132 | 0 | 0.565631466 |
| Phenylalanine | 'Nucleotide/Pyrimidine metabolism' | 't=' | 0.009613 | 0 | 0.741825516 |
| Creatine | 'Amino acids metabolism/Thr, Met, Asp/amino acid | 't=' | 0.014734 | 0 | 0.682009457 |
| Glycocyamine | 'Vitamins/B6' | t= | 0.022726 | 0 | 0.775619138 |
| Nicotinamide | 'Amino Acid' | mannW | 0.00293 | 0 | 0.741023861 |
| Glutaconic acid | 'Amino sugar and nucleotide sugar metabolism' | mannW | 0.031272 | 0.040816 | 0.707334856 |
| Valine | 'Nucleic Acid' | 't= | 0.005001 | 0 | 0.661098811 |
| Glutamine | 'Nucleotide/Purine metabolism' | 't=' | 0.013866 | 0 | 0.803605338 |
| Acetylglucosamine | 'Glycolysis/TCA' | mannW | 0.003558 | 0 | 0.816669194 |
| Kynurenine | 'Amino Acid' | mannW | 0.014931 | 0 | 0.608598323 |
| Neopterin | 'Aminobenzoate degradation' | mannW | 0.001055 | 0 | 0.654332771 |
| Glutaric acid | 'Sugar/Galactose' | mannW | 0.004882 | 0 | 0.477184717 |
| 6-Hydroxynicotinic acid | 'Arginine and proline metabolism' | 't=' | 0.027631 | 0.040816 | 1.295270632 |
| Mannose | 'Fatty acid metabolism' | 't=' | 0.004282 | 0 | 0.670589403 |
| Galactonic acid | 'TCA Cycle' | mannW | 0.00705 | 0 | 0.601130474 |
| 2HG | 'Tryptophan Cycle' | mannW | 0.024211 | 0 | 0.502616867 |
| 4-Hydroxy-3-methylbenzoic acid | 'Pyrrolidines' | 't!=*' | 0.000554 | 0 | 0.573389215 |

TABLE 1-continued

| Most significant metabolites. | | | | | |
|---|---|---|---|---|---|
| Measurements | Pathway | Test | p-Value | FDR | ASD/NT Mean |
| 2-Aminoadipic acid | 'organic acid' | mannW | 0.00293 | 0 | 0.492050115 |
| Acetylornithine | 'Nucleotide/Purine metabolism' | mannW | 0.019601 | 0 | 0.594120759 |
| Ethylmalonic acid | 'Sugar' | mannW | 0.005195 | 0.020408 | 0.741917119 |
| Tryptamine | 'Phenylalanine metabolism' | mannW | 0.003794 | 0 | 0.614887692 |
| Picolinic acid | 'Phenylalanine, tyrosine and tryptophan biosynthesis' | 't=' | 0.001176 | 0 | 0.576922959 |
| 5-Hydroxytrypt-ophan | '4-O-Methylated catecholamine metabolite' | 't=' | 0.008002 | 0 | 0.70905987 |

Test refers to the type of statistical test that was used. "t=" refers to the Student's t-test, "t!=" refers to the Welch's test, "t!=*" refers to the Welch's test without the normality criteria being met, and "mannW" refers to the Mann-Whitney U test.

Example 3: Search for Combinations of Metabolites to Best Differentiate the Two Groups of Children False Discovery Methods were used to search for combinations of metabolites that best differentiated the two groups of children. An exhaustive search was performed with the 26 most significant metabolites, using combinations of 1, 2, 3, 4, and 5 metabolites. In the tables below, the 15 best individual metabolites were listed, followed by the 15 best combinations of 2 metabolites, followed by the 15 best combinations of 3 metabolites, followed by the 15 best combinations of 4 metabolites, and finally the 15 best combinations of 5 metabolites. "Best" was defined by the metabolites being able to predict if a child had ASD or not. In other words, sensitivity and specificity were computed, and the best metabolites were those that maximized the sensitivity and specificity. Tables 1-6 comprise the best of top 1-5 combinations.

The most promising candidates were the following two combinations of five metabolites, as they resulted in misclassification errors of 13-17%:

(1) the combination of Glycocyamine; 6-Hydroxynicotinic acid; 4-Hydroxy-3-methylbenzoic acid; Acetylornithine; Tryptamine; and (2) the combination of Glycocyamine; Glutaconic acid; 6-Hydroxynicotinic acid; 4-Hydroxy-3-methylbenzoic acid; Acetylornithine.

Also, there are some metabolites which appear several times:

4-Hydroxy-3-methylbenzoic acid, which according HMDB, belongs to a class of organic compounds known as hydroxybenzoic acid derivatives. It is slightly soluble in water and a weakly acidic compound based on its pKa.

Glycocyamine, which according to HMDB, is a metabolite in the Urea cycle and metabolism of amino groups. It is also a precursor of creatine.

Glutaconic acid, which according to HMDB, has been detected in the urine if individuals with inborn errors of metabolism. In high levels, it can act as an acidogen, a neurotoxin, and a metabotoxin. This can lead to several disorders especially in babies.

TABLE 2

| Top 1 | | |
|---|---|---|
| Metabolites | Type I Error | Type II Error |
| 4-Hydroxy-3-methylbenzoic acid | 26.923% | 26.087% |
| Tyrosine | 34.615% | 30.435% |
| Tryptamine | 38.462% | 34.783% |
| Nicotinamide | 34.615% | 30.435% |
| Acetylcarnitine | 26.923% | 26.087% |
| Picolinic acid | 26.923% | 34.783% |
| Glutaric acid | 34.615% | 30.435% |
| 2-Aminoadipic acid | 30.769% | 34.783% |
| Glutamine | 38.462% | 43.478% |
| Kynurenine | 42.308% | 39.130% |
| Acetylglucosamine | 38.462% | 34.783% |
| 4-Imidazoleacetic acid | 34.615% | 34.783% |
| Ethylmalonic acid | 26.923% | 26.087% |
| Mannose | 34.615% | 34.783% |
| 5-Hydroxytryptophan | 34.615% | 30.435% |

TABLE 3

| Top 2 | | |
|---|---|---|
| Metabolites | Type I Error | Type II Error |
| 4-Hydroxy-3-methylbenzoic acid; Picolinic acid | 30.769% | 26.087% |
| 6-Hydroxynicotinic acid; Picolinic acid | 26.923% | 21.769% |
| 4-Hydroxy-3-methylbenzoic acid; Ethylmalonic acid | 26.087% | 19.231% |
| 4-Hydroxy-3-methylbenzoic acid; Tryptamine | 19.231% | 17.391% |
| Mannose; 4-Hydroxy-3-methylbenzoic acid | 23.077% | 30.435% |
| 4-Hydroxy-3-methylbenzoic acid; 5-Hydroxytryptophan | 23.077% | 26.087% |
| Acetylglucosamine; 4-Hydroxy-3-methylbenzoic acid | 26.923% | 26.087% |
| Glutaric acid; 4-Hydroxy-3-methylbenzoic acid | 34.615% | 34.783% |
| Tyrosine; 4-Hydroxy-3-methylbenzoic acid | 26.923% | 26.087% |
| Nicotinamide; 4-Hydroxy-3-methylbenzoic acid | 19.231% | 26.087% |
| 4-Hydroxy-3-methylbenzoic acid; 2-Aminoadipic acid | 23.077% | 21.739% |
| Glutamine; 4-Hydroxy-3-methylbenzoic acid | 26.923% | 26.087% |
| Tyrosine; Nicotinamide | 34.615% | 30.435% |
| Kynurenic acid; 4-Hydroxy-3-methylbenzoic acid | 30.769% | 26.087% |
| Glutaric acid; Tryptamine | 34.615% | 34.783% |

TABLE 4

| Top 3 | | |
|---|---|---|
| Metabolites | Type I Error | Type II Error |
| Tyrosine; Nicotinamide; 4-Hydroxy-3-methylbenzoic acid | 19.231% | 21.739% |
| Acetylglucosamine; 4-Hydroxy-3-methylbenzoic acid; Tryptamine | 15.385% | 17.391% |
| Acetylglucosamine; Neopterin; 4-Hydroxy-3-methylbenzoic acid | 26.923% | 26.087% |
| Glutaconic acid; Mannose; 4-Hydroxy-3-methylbenzoic acid | 23.077% | 26.087% |
| Tyrosine; Creatine; 4-Hydroxy-3-methylbenzoic acid | 19.231% | 21.739% |
| Nicotinamide; 4-Hydroxy-3-methylbenzoic acid; 5-Hydroxytryptophan | 23.077% | 21.739% |
| Nicotinamide; 4-Hydroxy-3-methylbenzoic acid; Tryptamine | 19.231% | 17.391% |
| Glutaconic acid; 4-Hydroxy-3-methylbenzoic acid; Tryptamine | 19.231% | 17.391% |
| 4-Hydroxy-3-methylbenzoic acid; 2-Aminoadipic acid; 5-Hydroxytryptophan | 19.231% | 17.391% |
| Nicotinamide; Acetylglucosamine; 4-Hydroxy-3-methylbenzoic acid | 19.231% | 17.391% |
| Glycocyamine; 4-Hydroxy-3-methylbenzoic acid; Tryptamine | 15.385% | 21.739% |
| 6-Hydroxynicotinic acid; 4-Hydroxy-3-methylbenzoic acid; Tryptamine | 23.077% | 21.739% |
| Tyrosine; 6-Hydroxynicotinic acid; 4-Hydroxy-3-methylbenzoic acid | 26.923% | 21.739% |
| Creatine; Glutaconic acid; 4-Hydroxy-3-methylbenzoic acid | 23.077% | 21.739% |
| Nicotinamide; Glutaric acid; 4-Hydroxy-3-methylbenzoic acid | 23.077% | 26.087% |

TABLE 5

| Top 4 | | |
|---|---|---|
| Metabolites | Type I Error | Type II Error |
| Glycocyamine; 4-Hydroxy-3-methylbenzoic acid; Acetylornithine; Tryptamine | 11.538% | 17.391% |
| Glycocyamine; Acetylglucosamine; 6-Hydroxynicotinic acid; 4-Hydroxy-3-methylbenzoic acid | 23.077% | 21.739% |
| Glycocyamine; 6-Hydroxynicotinic acid; 4-Hydroxy-3-methylbenzoic acid; Tryptamine | 19.231% | 17.391% |
| 6-Hydroxynicotinic acid; 4-Hydroxy-3-methylbenzoic acid; Acetylornithine; Tryptamine | 19.231% | 13.043% |
| Acetylglucosamine; 6-Hydroxynicotinic acid; 4-Hydroxy-3-methylbenzoic acid; Acetylomithine | 19.231% | 21.739% |
| Tyrosine; Creatine; Nicotinamide; 4-Hydroxy-3-methylbenzoic acid | 15.385% | 17.391% |
| Tyrosine; Nicotinamide; 4-Hydroxy-3-methylbenzoic acid; 5-Hydroxytryptophan | 19.231% | 21.739% |
| Tyrosine; Nicotinamide; Acetylglucosamine; 4-Hydroxy-3-methylbenzoic acid | 19.231% | 17.391% |
| Tyrosine; Nicotinamide; Valine; 4-Hydroxy-3-methylbenzoic acid | 19.231% | 21.739% |
| Tyrosine; Nicotinamide; 4-Hydroxy-3-methylbenzoic acid; Picolinic acid | 19.231% | 21.739% |
| Glycocyamine; 4-Hydroxy-3-methylbenzoic acid; Tryptamine; 5-Hydroxytryptophan | 15.385% | 17.391% |
| Glycocyamine; Acetylglucosamine; 4-Hydroxy-3-methylbenzoic acid; Tryptamine | 15.385% | 17.391% |
| Tyrosine; Glutamine; 4-Hydroxy-3-methylbenzoic acid; 5-Hydroxytryptophan | 23.077% | 26.087% |
| Tyrosine; Glycocyamine; 4-Hydroxy-3-methylbenzoic acid; Tryptamine | 23.077% | 13.043% |
| Glycocyamine; 4-Hydroxy-3-methylbenzoic acid; Tryptamine; Picolinic acid | 19.231% | 21.739% |

TABLE 6

| Top 5 | | |
|---|---|---|
| Metabolites | Type I Error | Type II Error |
| Glycocyamine; Acetylglucosamine; 4-Hydroxy-3-methylbenzoic acid; Acetylomithine; Tryptamine | 11.538% | 13.043% |
| Glycocyamine; 6-Hydroxynicotinic acid; 4-Hydroxy-3-methylbenzoic acid; Acetylomithine; Tryptamine | 15.385% | 13.043% |
| Glycocyamine; Acetylglucosamine; 4-Hydroxy-3-methylbenzoic acid; Tryptamine; 5-Hydroxytryptophan | 15.385% | 13.043% |
| Glycocyamine; Nicotinamide; Acetylglycosamine; 6-Hydroxynicotinic acid; 4-Hydroxy-3-methylbenzoic acid | 23.077% | 21.739% |
| Creatine; Glycocyamine; Acetylglucosamine; 6-Hydroxynicotinic acid; 4-Hydroxy-3-methylbenzoic acid | 23.077% | 26.087% |
| Glycocyamine; 6-Hydroxynicotinic acid; Mannose; 4-Hydroxy-3-methylbenzoic acid; Tryptamine | 19.231% | 21.739% |
| Glycocyamine; Glutaconic acid; 4-Hydroxy-3-methylbenzoic acid; Acetylomithine; Tryptamine | 15.385% | 13.043% |
| Tyrosine; Glycocyamine; 6-Hydroxynicotinic acid; 4-Hydroxy-3-methylbenzoic acid; Tryptamine | 19.231% | 17.391% |
| Glycocyamine; Nicotinamide; Glutaconic acid; Mannose; 4-Hydroxy-3-methylbenzoic acid | 19.231% | 21.739% |
| Glycocyamine; Glutaric acid; 6-Hydroxynicotinic acid; 4-Hydroxy-3-methylbenzoic acid; Tryptamine | 19.231% | 17.391% |
| Glycocyamine; 6-Hydroxynicotinic acid; 4-Hydroxy-3-methylbenzoic acid; 2-Aminoadipic acid; Tryptamine | 19.231% | 13.043% |
| Glycocyamine; 6-Hydroxynicotinic acid; 4-Hydroxy-3-methylbenzoic acid; Tryptamine; Picolinic acid | 19.231% | 21.739% |
| Glycocyamine; 6-Hydroxynicotinic acid; Mannose; 4-Hydroxy-3-methylbenzoic acid; 5-Hydroxytryptophan | 19.231% | 13.043% |
| Tyrosine; Glycocyamine; 4-Hydroxy-3-methylbenzoic acid; Acetylornithine; Tryptamine | 15.385% | 17.391% |
| Glycocyamine; Glutamine; 6-Hydroxynicotinic acid; 4-Hydroxy-3-methylbenzoic acid; Tryptamine | 19.231% | 21.739% |

Example 4: Search for Further Combinations of Metabolites to Best Differentiate Between the Two Different Groups of Children In case the pre-selection process is too selective, all of the metabolites were analyzed to find the best combinations of metabolites. It was found that these metabolites provided more accurate separations.

The most promising combinations of metabolites for the entire group of metabolites were two groups of five metabolites with errors ranging from 3-8%: (1) Anthranilic acid, N-Acetylethanolamine, Stearic acid, 4-Hydroxy-3-methylbenzoic acid, and Glyceric acid and (2) N-Acetylethanolamine, 4-Pyridoxic acid, Stearic acid, 4-Hydroxy-3-methylbenzoic acid, and 3-Aminoadipic acid.

There are some metabolites that also appear several times:

4-Hydroxy-3-methylbenzoic acid which is discussed in the above section.

N-Acetylethanolamine which, according to HMDB, belongs to a class of organic compounds known as carboxylic acid esters.

4-Pyridoxic acid which, according to HMDB, is a catabolic product of the vitamin B6. The levels of measurement in urine are higher in males than in females. They are reduced in people with riboflavin deficiency.

Stearic acid which, according to HMDB, is a type of saturated fatty acid that is found in animal and vegetable fats and oils.

The results are shown in Tables 7-11.

TABLE 7

Top 1

| Metabolite | Type I Error | Type II Error |
|---|---|---|
| 4-Hydroxy-3-methylbenzoic acid | 26.923% | 26.087% |
| Capric acid | 38.462% | 39.130% |
| Tyrosine | 34.615% | 30.435% |
| Tryptamine | 34.615% | 34.783% |
| Nicotinamide | 34.615% | 30.435% |
| Acetylcarnitine | 26.923% | 26.087% |
| Amino valerate | 38.462% | 26.087% |
| Hydroxyproline | 38.462% | 39.130% |
| Picolinic acid | 26.923% | 34.783% |
| Glutaric acid | 34.615% | 30.435% |
| HIAA | 38.462% | 39.130% |
| 2-Aminoadipic acid | 30.769% | 34.783% |
| Glutamine | 38.462% | 43.478% |
| Kynurenine | 42.308% | 39.130% |
| Alpha-KG/Adipic acid | 42.308% | 34.783% |

TABLE 8

Top 2

| Metabolite | Type I Error | Type II Error |
|---|---|---|
| Acetylglucosamine; 4-Hydroxy-3-methylbenzoic acid | 26.923% | 26.087% |
| 4-Hydroxy-3-methylbenzoic acid; Inosine | 26.923% | 30.435% |
| 4-Hydroxy-3-methylbenzoic acid; Picolinic acid | 30.769% | 26.087% |
| Gentisic acid; 4-Hydroxy-3-methylbenzoic acid | 23.077% | 21.739% |
| 4-Hydroxy-3-methylbenzoic acid; Ethylmalonic acid | 19.231% | 26.087% |
| 4-Aminobutyric acid; 4-Hydroxy-3-methylbenzoic acid | 34.615% | 34.783% |
| Trehalose; 4-Hydroxy-3-methylbenzoic acid | 26.923% | 30.435% |
| Acetylglucosamine; Urocanic acid | 26.923% | 21.739% |
| Phosphocreatine; 4-Hydroxy-3-methylbenzoic acid | 26.923% | 30.435% |
| Histidine; 4-Hydroxy-3-methylbenzoic acid | 26.923% | 30.435% |
| Allopurinol; 4-Hydroxy-3-methylbenzoic acid | 34.615% | 30.435% |
| 4-Hydroxy-3-methylbenzoic acid; 5-Hydroxytryptophan | 23.077% | 26.087% |
| 4-Imidazoleacetic acid; 4-Hydroxy-3-methylbenzoic acid | 30.769% | 26.087% |
| Glutaric acid; 4-Hydroxy-3-methylbenzoic acid | 34.615% | 34.783% |
| Phenylalanine; 4-Hydroxy-3-methylbenzoic acid | 23.077 | 21.739% |

TABLE 9

Top 3.

| Metabolite | Type I Error | Type II Error |
|---|---|---|
| Tyrosine; 4-Hydroxy-3-methylbenzoic acid; GA3P | 23.077% | 26.087% |
| Phenylalanine; 4-Hydroxy-3-methylbenzoic acid; GA3P | 23.077% | 26.087% |
| NAD; Mannose; 4-Hydroxy-3-methylbenzoic acid | 19.231% | 21.739% |
| Nicotinamide; Pipecolinic acid; 4-Hydroxy-3-methylbenzoic acid | 15.385% | 13.043% |
| Allopurinol; 4-Hydroxy-3-methylbenzoic acid; Picolinic acid | 26.923% | 26.087% |
| Tyrosine; Mannose; 4-Hydroxy-3-methylbenzoic acid | 26.923% | 26.087% |
| 4-Aminobutyric acid; 4-Hydroxy-3-methylbenzoic acid; Tryptamine | 23.077% | 21.739% |

TABLE 9-continued

Top 3.

| Metabolite | Type I Error | Type II Error |
|---|---|---|
| Amino valerate; N-Acetylneuraminic acid; 4-Hydroxy-3-methylbenzoic acid | 23.077% | 21.739% |
| Mannose; 4-Hydroxy-3-methylbenzoic acid; Picolinic acid | 26.923% | 26.087% |
| Tyrosine; 3-Methyl-2-oxovaleric acid; 4-Hydroxy-3-methylbenzoic acid | 23.077% | 26.087% |
| Tyrosine; Nicotinamide; 4-Hydroxy-3-methylbenzoic acid | 19.231% | 21.739% |
| 3-Methyl-2-oxovaleric acid; 4-Hydroxy-3-methylbenzoic acid; Picolinic acid | 26.923% | 26.087% |
| Nicotinamide; 4-Hydroxy-3-methylbenzoic acid; Picolinic acid | 23.077% | 21.739% |
| Agmatine; Glutaric acid; 4-Hydroxy-3-methylbenzoic acid | 19.231% | 17.391% |
| Tyrosine; 4-Pyridoxic acid; 4-Hydroxy-3-methylbenzoic acid | 26.923% | 30.435% |

TABLE 10

Top 4

| Metabolite | Type I Error | Type II Error |
|---|---|---|
| Amino valerate; N-Acetylneuraminic acid; Urocanic acid; 4-Hydroxy-3-methylbenzoic acid | 11.538% | 8.6957% |
| N-Acetylethanolamine; 4-Pyridoxic acid; Citrulline; 4-Hydroxy-3-methylbenzoic acid | 11.538% | 13.043% |
| Nicotinamide; Indole-3-acetic acid; Mannose; 4-Hydroxy-3-methylbenzoic acid | 19.231% | 13.043% |
| N-Acetylethanolamine; Glycocyamine; 4-Hydroxy-3-methylbenzoic acid; Tryptamine | 11.538% | 17.391% |
| Tyrosine; N-Acetylethanolamine; Nonadecanoic acid; 4-Hydroxy-3-methylbenzoic acid | 11.538% | 13.043% |
| Indole-3-acetic acid; Guanosine; 4-Hydroxy-3-methylbenzoic acid; Tryptamine | 15.385% | 17.391% |
| N-Acetylethanolamine; 4-Pyridoxic acid; Stearic acid; 4-Hydroxy-3-methylbenzoic acid | 15.385% | 17.391% |
| Anthranilic acid; N-Acetylethanolamine; Stearic acid; 4-Hydroxy-3-methylbenzoic acid | 11.538% | 13.043% |
| N-Acetylethanolamine; 2HG; 4-Hydroxy-3-methylbenzoic acid; Picolinic acid | 23.077% | 21.739% |
| Tyrosine; N-Acetylethanolamine; alpha-KG/Adipic acid; 4-Hydroxy-3-methylbenzoic acid | 23.077% | 30.435% |
| N-Acetylethanolamine; Allopurinol; 4-Hydroxy-3-methylbenzoic acid; Picolinic acid | 23.077% | 13.043% |
| Amino valerate; Stearic acid; 4-Hydroxy-3-methylbenzoic acid; Phenylacetic acid | 19.231% | 21.739% |
| Anthranilic acid; Tyrosine; N-Acetylethanolamine; 4-Hydroxy-3-methylbenzoic acid | 15.385% | 13.043% |
| Tyrosine; N-Acetylethanolamine; 4-Pyridoxic acid; 4-Hydroxy-3-methylbenzoic acid | 15.385% | 17.391% |
| Anthranilic acid; N-Acetylethanolamine; Allopurinol; 4-Hydroxy-3-methylbenzoic acid | 15.385% | 17.391% |

TABLE 11

Top 5

| Metabolite | Type I Error | Type II Error |
|---|---|---|
| Anthranilic acid; N-Acetylethanolamine; Stearic acid; 4-Hydroxy-3-methylbenzoic acid; Glyceric acid | 7.6923% | 4.3478% |
| N-Acetylethanolamine; 4-Pyridoxic acid; Stearic acid; 4-Hydroxy-3-methylbenzoic acid; 3-Aminoadipic acid | 3.8462% | 8.6957% |
| N-Acetylethanolamine; 4-Pyridoxic acid; Citrulline; 4-Hydroxy-3-methylbenzoic acid; Glutamic acid | 7.6923% | 8.6957% |
| N-Acetylethanolamine; 4-Pyridoxic acid; Citrulline; 4-Hydroxy-3-methylbenzoic acid; 3-Methy1-2-oxovaleric acid | 7.6923% | 8.6957% |

TABLE 11-continued

| Top 5 | | |
|---|---|---|
| Metabolite | Type I Error | Type II Error |
| N-Acetylethanolamine; 4-Pyridoxic acid; Citrulline; 4-Hydroxy-3-methylbenzoic acid; Mannose | 7.6923% | 8.6957% |
| N-Acetylethanolamine; 4-Pyridoxic acid; Citrulline; 4-Hydroxy-3-methylbenzoic acid; 2-Hydroxybutyric acid/Malonic acid | 7.6923% | 8.6957% |
| Anthranilic acid; N-Acetylethanolmine; Stearic acid; 4-Hydroxy-3-methylbenzoic acid; 1-Methylhistidine | 7.6923% | 8.6957% |
| Anthranilic acid; N-Acetylethanolamine; Stearic acid; 4-Hydroxy-3-methylbenzoic acid; Cytidine | 7.6923% | 8.6957% |
| N-Acetylethanolamine; Allopurinol; 4-Hydroxy-3-methylbenzoic acid; Picolinic acid; 4-Pyridoxic acid | 7.6923% | 8.6957% |
| Anthranilic acid; Tyrosine; N-Acetylethanolamine; 4-Hydroxy-3-methylbenzoic acid; Imidazole | 7.6923% | 8.6957% |
| Amino valerate; N-Acetylneuraminic acid; Urocanic acid; 4-Hydroxy-3-methylbenzoic acid; Decanoylcarnitine | 11.538% | 8.6957% |
| N-Acetylethanolamine; 4-Pyridoxic acid; Stearic acid; 4-Hydroxy-3-methylbenzoic acid; Nicotinamide | 7.6923% | 8.6957% |
| Amino valerate; Stearic acid; 4-Hydroxy-3-methylbenzoic acid; Phenylacetic acid; Acetylglucosamine | 11.538% | 8.6957% |
| Tyrosine; N-Acetylethanolamine; 4-Pyridoxic acid; 4-Hydroxy-3-methylbenzoic acid; Stearic acid | 11.538% | 8.6957% |
| N-Acetylethanolamine; Glycocyamine; 4-Hydroxy-3-methylbenzoic acid; Tryptamine; 4-Methylvaleric acid/Hexanoic acid | 11.538% | 8.6957% |

Example 5: Sample Collection

Urine samples were collected at home. Most were collected as first-morning urine samples. However, for some children spot urines were collected due to difficulties with urine collection. Samples were immediately placed in a freezer. Samples were picked up within 3 days, transported on dry ice, and stored in a −80° C. freezer.

Once all samples were collected from all patients, they were tested. The samples were collected during the same time period, so the difference in storage times between the two groups was small, which also helps to minimize differences since even at −80° C. there is a small degradation of sample quality (estimated at 2%/year).

Example 6: Methodology of Measuring Metabolites (by Arizona Metabolomics Laboratory, AML)

Sample Accessioning: Following reception, samples were inventoried in a unique sample box (named by date+PI) and immediately stored at −80° C. Sample information including PI, institution, sample description, number of samples, and date of arrival were recorded in our working list and analysis progress was updated daily. All samples were maintained at −80° C. until processed.

Sample Preparation: Frozen urine samples were thawed overnight at 4° C. and vortexed for 5 seconds. Then 50 μL aliquot of each sample was transferred to a 2 mL Eppendorf vial. To precipitate proteins, 500 μL MeOH was added. In addition, 50 μL internal standard solution (1×PBS containing 1810.5 μM $^{13}$C3-Lactate and 142 μM $^{13}$C5-Glutamic Acid) was added. The mixtures were vortexed for 5 seconds and stored at −20° C. for 20 minutes, followed by centrifugation at 14,000 rpm for 10 minutes. After that, 450 μL of supernatant was collected into a new 2 mL Eppendorf vial and dried in a CentriVap Concentrator at 37° C. for 120 minutes.

The dried samples were reconstituted with 150 μL of 40% PBS/60% ACN followed by 5 seconds of vortexing. The reconstituted samples were centrifuged again at 14,000 rmp for 10 minutes, and 100 μL of supernatant of each sample was collected into a LC vial for HILIC/UPLC-MS/MS analysis using both positive and negative ion mode ESI. All the remaining 50 μL supernatant in each sample was pooled together and used as the quality-control (QC).

QC and Blank: The QC sample was analyzed once every 10 study samples serving as a technical replicate throughout the data set. This allowed for instrument performance monitoring and chromatographic aligning. Extracted methanol samples served as process blanks. Table 12 describe these QC samples. Instrument variability was determined by calculating the coefficient of variation (CV) for the QC. Experimental samples were randomized across the platform run with QC samples spaced evenly among the injections, as outlined in FIG. 1.

TABLE 12

| Description of AML QC and Blank Samples | | |
|---|---|---|
| Type | Description | Purpose |
| QC | Pool created by taking a small aliquot from every study sample. | Assess the matrix effect on the AML process and distinguish biological variability from process variability. |
| Blank | Aliquot of solvents used in extraction. | ProcessBlank used to assess the contribution to compound signals from the process. |

Ultrahigh Performance Liquid Chromatography-Triple Quadrupole Mass Spectroscopy (UPLC-QQQ MS): All LC-MS/MS experiments were performed on an Agilent 1290 UPLC-6490 QQQ-MS (Santa Clara, CA) system. Each sample was injected twice, 10 μL for analysis using negative ionization mode and 4 μL for analysis using positive ionization mode. Both chromatographic separations were performed in hydrophilic interaction chromatography (HILIC) mode on a Waters XBridge BEH Amide column (150×2.1 mm, 2.5 μm particle size, Waters Corporation, Milford, MA). The flow rate was 0.3 mL/min, auto-sampler temperature was kept at 4° C., and the column compartment was set at 40° C. The mobile phase was composed of Solvents A (10 mM ammonium acetate, 10 mM ammonium hydroxide in 95% $H_2O$/5% ACN) and B (10 mM ammonium acetate, 10 mM ammonium hydroxide in 95% ACN/5% $H_2O$). After the initial 1 min isocratic elution of 90% B, the percentage of Solvent B decreased to 40% at t=11 min. The composition of Solvent B maintained at 40% for 4 min (t=15 min), and then the percentage of B gradually went back to 90%, to prepare for the next injection. The mass spectrometer is equipped with an electrospray ionization (ESI) source. Targeted data acquisition was performed in multiple-reaction-monitoring (MRM) mode. 118 and 160 MRM transitions in negative and positive mode, respectively (278 transitions in total) were monitored. The whole LC-MS system was controlled by Agilent Masshunter Workstation software (Santa Clara, CA). The extracted MRM peaks were integrated using Agilent MassHunter Quantitative Data Analysis (Santa Clara, CA).

Data Extraction and Compound Identification: Raw data was extracted, peak-identified, and QC processed using Agilent QQQ Quantitative Analysis software. Compounds were identified by comparison to internal library entries of purified standards. AML maintains a library based on authenticated standards that contains the retention time, mass to charge ratio (m/z), chromatographic data, and MRM parameters on all molecules present in the library. Furthermore, biochemical identifications were based on two criteria: retention time within a narrow RT window of the proposed identification, and the MRM parameters (precursor and product ion pairs). About 300 commercially-available purified standard compounds have been acquired and registered into our library.

Curation: A variety of curation procedures were carried out to ensure that a high quality data set was made available for statistical analysis and data interpretation. The QC and curation processes were designed to ensure accurate and consistent identification of true chemical entities, and to remove those representing system artifacts, mis-assignments, and background noise. AML data analysts use proprietary visualization and interpretation software to confirm the consistency of peak identification among the various samples. Library matches for each compound were double-checked for each sample and corrected if necessary.

Metabolite Quantification and Data Normalization: Peaks were quantified using area-under-the-curve. If necessary, a data normalization step was performed to correct variation using the QC sample. Essentially, each compound in a certain sample was corrected using the averaged intensity of this compound in the two QC data covering this sample according the MS run sequence.

Example 7: Univariate Analysis of Short Chain Fatty Acids (SCFA) in Serum

Each of a set of 5 variables (Table 13) were analyzed using the Anderson-Darling test for normality. Dependent on if the normality assumption was accepted or rejected; the samples were either subjected to an F-test or a Kolmogorov-Smirnov test. The purpose of the F-test was to determine if the samples had the same variance and the Kolmogorov-Smirnov test would ascertain if the samples had the same or different distributions. Depending on the circumstances, either a Mann-Whitney or t-test would ultimately be performed to determine whether the two sample sets from each cohort were likely derived from the same distribution. The mean, standard deviation and ASD/TD ratio was subsequently determined for each variable as well.

TABLE 13

| Variable | TD Mean | ASD Mean | TD Standard Deviation | ASD Standard Deviation | Ratio | Optimized Univariate Test | P-value |
|---|---|---|---|---|---|---|---|
| C 8:0 | 7.30E−05 | 7.47E−05 | 4.56742E−05 | 2.786E−05 | 1.02 | Mann-Whitney | 0.318 |
| Lactate | 0.131 | 0.130 | 0.050 | 0.035 | 0.99 | Equal Variance t-test | 0.917 |
| C 9:0 | 8.43E−05 | 8.60E−05 | 6.051E−05 | 3.994E−05 | 1.02 | Mann-Whitney | 0.371 |
| C 10:0 | 3.196E−05 | 3.58E−05 | 1.109E−05 | 1.610E−05 | 1.12 | Unequal Variance t-test | 0.284 |
| Succinate | 6.70E−04 | 7.329E−04 | 1.41851E−04 | 0.00012009 | 1.09 | Equal Variance t-test | 0.076 |

The p-values obtained for each optimized test were all greater than 0.05 for all samples. The variables that were determined to have a significance less than 0.05 are included in the Table 14 below, along with their false discovery rate.

TABLE 14

| Name | TD Mean | TD SD | ASD Mean | ASD SD | ASD/ TD Ratio | Test | P-value | FDR |
|---|---|---|---|---|---|---|---|---|
| 73.0 @ 27.53799:1 | 58974.97 | 53492.06 | 99077.67 | 58412.46 | 1.68 | Mann-Whitney | 0.00 | 0.00 |
| 73.0 @ 27.53799:2 | 58974.97 | 53492.06 | 99077.67 | 58412.76 | 1.68 | Mann-Whitney | 0.00 | 0.00 |
| 79.0 @ 15.390011 | 73618.43 | 29393.41 | 88887.13 | 29593.95 | 1.21 | Mann-Whitney | 0.04 | 0.38 |
| Urea, 2TBDMS derivative | 9447024.33 | 4858320.94 | 11175344.50 | 3552783.26 | 1.18 | Mann-Whitney | 0.03 | 0.07 |
| 200.2 @ 15.739994 | 73271.27 | 33717.02 | 96855.43 | 31037.17 | 1.32 | Equal Variance t-test | 0.01 | 0.00 |
| D-Pyroglutamic acid, 2TBDMS derivative | 611672.70 | 216141.27 | 728927.93 | 210059.63 | 1.19 | Equal Variance t-test | 0.04 | 0.31 |
| 221.1 @ 24.365997 | 38004.37 | 14721.00 | 46568.73 | 17929.32 | 1.23 | Mann-Whitney | 0.03 | 0.34 |
| L-Leucine, 2TBDMS derivative | 221232.00 | 98700.96 | 288365.93 | 124053.34 | 1.30 | Mann-Whitney | 0.03 | 0.22 |
| Uric acid, 4TBDMS derivative | 779775.43 | 473545.79 | 914253.27 | 421072.26 | 1.17 | Mann-Whitney | 0.04 | 0.46 |
| 73.1 @ 25.61099:2 | 392615.07 | 233835.26 | 463765.60 | 214048.34 | 1.18 | Mann-Whitney | 0.03 | 0.10 |
| 55.1 @ 22.708988 | 205159.83 | 43930.26 | 240123.10 | 59517.13 | 1.17 | Equal Variance t-test | 0.01 | 0.00 |
| (2R)-Pyrrolidine-1,2-dicarboxylic acid, bis(tert-butyldimethylsilyl) ester | 327365.13 | 214298.31 | 353304.00 | 103093.66 | 1.08 | Mann-Whitney | 0.04 | 0.44 |
| 73.0 @ 22.708988:1 | 534917.33 | 242316.65 | 724902.33 | 273096.51 | 1.36 | Mann-Whitney | 0.01 | 0.00 |
| 91.0 @ 22.552 | 63493.40 | 37299.80 | 86670.10 | 47106.19 | 1.37 | Equal Variance t-test | 0.04 | 0.37 |
| 208.0 @ 27.66299 | 12564.67 | 4433.20 | 16618.20 | 6246.617 | 1.32 | Equal Variance t-test | 0.01 | 0.00 |
| 117.0 @ 22.706366 | 456554.97 | 251144.35 | 635264.20 | 354357.94 | 1.39 | Mann-Whitney | 0.01 | 0.00 |
| 207.0 @ 22.571007 | 28553.07 | 13146.32 | 36897.17 | 15938.63 | 1.29 | Mann-Whitney | 0.01 | 0.00 |
| 135.0 @ 22.708323 | 37391.47 | 18854.88 | 50629.23 | 17096.94 | 1.35 | Equal Variance t-test | 0.01 | 0.00 |
| 59.0 @ 10.075058 | 1363933.97 | 1673224.94 | 2465363.43 | 1876880.23 | 1.81 | Mann-Whitney | 0.01 | 0.00 |
| Tris(trimethylsilyl) carbamate El + 13.6804905 | 12336558.43 | 20448794.74 | 4828719.33 | 4222952.83 | 0.39 | Mann-Whitney | 0.03 | 0.08 |
| 101.0 @ 22.677 | 99211.90 | 54111.05 | 126025.90 | 58158.29 | 1.27 | Mann-Whitney | 0.05 | 0.58 |
| 86.0 @ 22.708006 | 54516.27 | 25444.99 | 67167.93 | 23429.13 | 1.23 | Mann-Whitney | 0.02 | 0.03 |
| 147.1 @ 24.37301:1 | 767740.63 | 338330.40 | 1026311.10 | 517986.25 | 1.34 | Mann-Whitney | 0.04 | 0.35 |
| 95.1 @ 19.337 | 263176.13 | 336790.36 | 159558.03 | 253219.69 | 0.61 | Mann-Whitney | 0.01 | 0.00 |
| L-Leucine, 2TBDMS derivative El + 15.377265 | 221542.80 | 115698.20 | 284676.97 | 127455.26 | 1.28 | Equal Variance t-test | 0.05 | 0.29 |
| 133.0 @ 22.702015 | 92699.13 | 65539.11 | 123577.10 | 76302.31 | 1.33 | Mann-Whitney | 0.01 | 0.00 |
| 117.0 @ 22.693932 | 426124.43 | 298058.95 | 644864.50 | 404545.22 | 1.51 | Mann-Whitney | 0.01 | 0.00 |
| 149.0 @ 22.703001 | 79044.37 | 43281.16 | 95694.27 | 38664.73 | 1.21 | Mann-Whitney | 0.04 | 0.48 |
| 231.1 @ 22.677 | 82740.07 | 49518.42 | 110864.97 | 58118.64 | 1.34 | Mann-Whitney | 0.05 | 0.52 |

TABLE 14-continued

| Name | TD Mean | TD SD | ASD Mean | ASD SD | ASD/ TD Ratio | Test | P- value | FDR |
|---|---|---|---|---|---|---|---|---|
| 100.0 @ 22.671011:1 | 80171.27 | 46797.89 | 104715.27 | 47870.59 | 1.31 | Equal Variance t-test | 0.05 | 0.51 |
| 105.0 @ 22.546011 | 58915.87 | 33700.51 | 87789.07 | 36961.27 | 1.49 | Mann-Whitney | 0.00 | 0.00 |
| 79.0 @ 12.970995 | 88886.13 | 73663.13 | 54411.10 | 51134.83 | 0.61 | Mann-Whitney | 0.04 | 0.39 |
| 86.0 @ 22.702015 | 52066.33 | 23408.17 | 65236.47 | 20269.82 | 1.25 | Equal Variance t-test | 0.02 | 0.03 |
| 261.2 @ 22.671011 | 68015.17 | 41082.42 | 92129.67 | 43592.74 | 1.35 | Mann-Whitney | 0.00 | 0.00 |
| 147.1 @ 25.61099:1 | 36874.43 | 19135.20 | 44088.80 | 17023.99 | 1.20 | Mann-Whitney | 0.04 | 0.58 |
| 57.1 @ 14.864994 | 607699.03 | 338450.58 | 710308.20 | 227120.05 | 1.17 | Mann-Whitney | 0.03 | 0.20 |
| 76.0 @ 14.86401 | 104972.80 | 82541.53 | 163267.77 | 110300.31 | 1.56 | Mann-Whitney | 0.04 | 0.39 |
| 105.0 @ 8.355344 | 591083.60 | 258170.88 | 723408.00 | 196976.33 | 1.22 | Mann-Whitney | 0.04 | 0.35 |
| 186.2 @ 14.86401:1 | 238143.20 | 163328.33 | 329542.03 | 215978.78 | 1.38 | Mann-Whitney | 0.04 | 0.48 |
| 111.1 @ 13.599963 | 32583.33 | 24371.45 | 25001.50 | 35160.44 | 0.77 | Mann-Whitney | 0.02 | 0.00 |
| 73.0 @ 19.385714 | 212606.47 | 95475.37 | 160940.33 | 102565.05 | 0.76 | Mann-Whitney | 0.02 | 0.28 |
| 63.0 @ 13.581986 | 101237.77 | 74407.93 | 70124.17 | 55426.60 | 0.69 | Mann-Whitney | 0.05 | 0.58 |
| 344.2 @ 24.364178 | 413257.10 | 213548.48 | 571716.60 | 337832.11 | 1.38 | Mann-Whitney | 0.03 | 0.26 |
| Uric acid, 4TBDMS derivative El + 25.61698 | 418913.50 | 260752.23 | 490842.17 | 225488.85 | 1.17 | Mann-Whitney | 0.03 | 0.29 |
| 74.1 @ 22.708006 | 112986.37 | 84484.89 | 146744.20 | 88376.71 | 1.30 | Mann-Whitney | 0.02 | 0.00 |
| 133.0 @ 14.864994 | 342837.47 | 161959.71 | 436085.27 | 178541.84 | 1.27 | Mann-Whitney | 0.03 | 0.13 |
| 99.0 @ 14.86401 | 339171.97 | 160723.11 | 403834.57 | 123414.90 | 1.19 | Mann-Whitney | 0.03 | 0.15 |
| 213.1 @ 14.86401 | 413793.67 | 173276.76 | 498296.90 | 136242.26 | 1.20 | Equal Variance t-test | 0.04 | 0.39 |
| 202.1 @ 24.467009 | 218405.30 | 214113.14 | 436966.33 | 458512.20 | 2.00 | Mann-Whitney | 0.03 | 0.17 |
| 303.2 @ 23.941008 | 31909.13 | 15745.77 | 39711.23 | 14643.48 | 1.24 | Mann-Whitney | 0.02 | 0.02 |
| Salicylic acid, 2TBDMS derivative | 366298.57 | 275138.43 | 548456.50 | 307291.71 | 1.50 | Mann-Whitney | 0.02 | 0.00 |
| 85.1 @ 22.708988 | 45346.63 | 17256.65 | 58697.10 | 29520.27 | 1.29 | unequal Variance t-test | 0.04 | 0.23 |
| 147.1 @ 17.786007 | 140161.00 | 69773.02 | 178347.47 | 46948.99 | 1.27 | Mann-Whitney | 0.04 | 0.28 |
| 73.0 @ 27.53799:3 | 19673.37 | 16047.74 | 27756.30 | 15690.04 | 1.41 | Mann-Whitney | 0.02 | 0.00 |
| 100.0 @ 14.867003 | 194366.53 | 127731.94 | 258648.93 | 80907.04 | 1.33 | unequal Variance t-test | 0.02 | 0.05 |
| 208.0 @ 26.41199 | 19784.70 | 20007.25 | 30206.47 | 19507.53 | 1.53 | Mann-Whitney | 0.01 | 0.00 |
| 73.1 @ 25.610992 | 345817.07 | 253457.59 | 433590.10 | 218655.39 | 1.25 | Mann-Whitney | 0.03 | 0.09 |
| 203.1 @ 22.671011 | 38158.40 | 29659.79 | 60188.73 | 31327.57 | 1.58 | Equal Variance t-test | 0.01 | 0.00 |
| 339.3 @ 22.671011 | 97651.60 | 89462.26 | 136643.00 | 72274.77 | 1.40 | Mann-Whitney | 0.02 | 0.00 |
| 73.0 @ 22.708988:2 | 184973.93 | 148104.50 | 268988.97 | 121867.40 | 1.45 | Mann-Whitney | 0.04 | 0.31 |
| 341.0 @ 27.543983 | 7145.17 | 6303.43 | 10977.10 | 6691.06 | 1.54 | Equal Variance t-test | 0.03 | 0.08 |
| 57.1 @ 16.153011 | 40073.97 | 27559.48 | 55739.57 | 30851.72 | 1.39 | Mann-Whitney | 0.03 | 0.06 |

TABLE 14-continued

| Name | TD Mean | TD SD | ASD Mean | ASD SD | ASD/ TD Ratio | Test | P-value | FDR |
|---|---|---|---|---|---|---|---|---|
| Heptasiloxane, 1,1,3,3,5,5,7,7,9,9, 11,11,13,13-tetradecamethyl-El + 26.413776 | 37694.33 | 39728.61 | 55867.97 | 31268.33 | 1.48 | Mann-Whitney | 0.01 | 0.00 |
| 208.0 @ 27.538107 | 8271.80 | 7397.20 | 13198.30 | 8050.48 | 1.60 | Mann-Whitney | 0.04 | 0.29 |

The following models were subsequently attained using FDA to maximize the AUROC for different numbers of metabolites. The model discovery protocol used for the SOFA analysis only examined the significant fatty acids. As with the urine metabolites, an optimized univiariate test was performed for each of the constituent variables. The 64 fatty acids determined to be significantly different (p-value<0.05) in the ASD and TD groups were then used for developing an FDA model (Table 15).

TABLE 15

| Number of Metabolites | Variable Combination | Fitted AUROC |
|---|---|---|
| 2 | 73.0@19.385714<br>105.0@22.546011 | 0.84 |
| 3 | 73.0@19.385714<br>105.0@22.546011<br>208.0@27.66299 | 0.88 |
| 4 | 73.0@19.385714<br>105.0@22.546011<br>208.0@27.66299<br>76.0@14.86401 | 0.90 |
| 5 | 73.0@19.385714<br>105.0@22.546011<br>208.0@27.66299<br>76.0@14.86401<br>207.0@22.571007 | 0.92 |

Example 8. Analysis of Whole Blood Metabolites

First, the univariate area under ROC curve (AUROC) was calculated for each metabolite individually. Metabolites with AUROC>=0.6 for analysis with FDA were accepted. In total, 66 metabolites met this criterion. An exhaustive search was performed over all combinations of up to five metabolites, fitting an FDA model to each combination of metabolites. For each number of metabolites, evaluate the top 1000 combinations by AUROC with leave-one-out cross-validation.

Details for the best combination with cross-validation for each number of metabolites are given in Table 16 below. The value β is the Type II error according to the fitted PDFs and is varied to obtain sensitivity (TPR) and specificity (TNR) at different classification thresholds.

TABLE 16

| Number of Metabolites | Metabolite Combination | Fitted AUROC | Cross-Validated Results β | TPR | TNR |
|---|---|---|---|---|---|
| 2 | 6-Hydroxynicotinic acid | 0.847 | 0.05 | 0.966 | 0.233 |
| | 2-Aminoadipic acid | | 0.10 | 0.931 | 0.400 |
| | | | 0.15 | 0.897 | 0.567 |
| | | | 0.20 | 0.793 | 0.700 |
| 3 | 2,3-Dihydroxybenzoic acid | 0.892 | 0.05 | 0.966 | 0.433 |
| | Cadaverine | | 0.10 | 0.862 | 0.600 |
| | Galactonic acid | | 0.15 | 0.828 | 0.733 |
| | | | 0.20 | 0.828 | 0.833 |
| 4 | 2,3-Dihydroxybenzoic acid | 0.92 | 0.05 | 0.931 | 0.600 |
| | 6-Hydroxynicotinic acid | | 0.10 | 0.897 | 0.700 |
| | 2-Aminoadipic acid | | 0.15 | 0.862 | 0.800 |
| | 13C5-15N-Glutamic acid | | 0.20 | 0.759 | 0.833 |
| 5 | 2,3-Dihydroxybenzoic acid | 0.932 | 0.05 | 0.966 | 0.733 |
| | 2-Aminoadipic acid | | 0.10 | 0.931 | 0.867 |
| | 13C5-15N-Glutamic acid | | 0.15 | 0.862 | 0.933 |
| | Methylmalonic acid<br>Levulinic acid | | 0.20 | 0.828 | 0.933 |

Among the combination of metabolites listed in Table 16, the five-metabolite model yielded the most accurate cross-validation results. This model is explored in further detail below.

At β=0.1, the Type I error is 0.136 (13.6%). The confusion matrix from cross-validation is:

| | Predicted ASD (n = 31) | Predicted TD (n = 28) | |
|---|---|---|---|
| Actual ASD (n = 29) | TP<br>27 | FN<br>2 | TPR<br>0.931 |
| Actual TD (n = 30) | FP<br>4 | TN<br>26 | TNR<br>0.867 |
| | PPV<br>0.871 | NPV<br>0.929 | |

Figure 2:
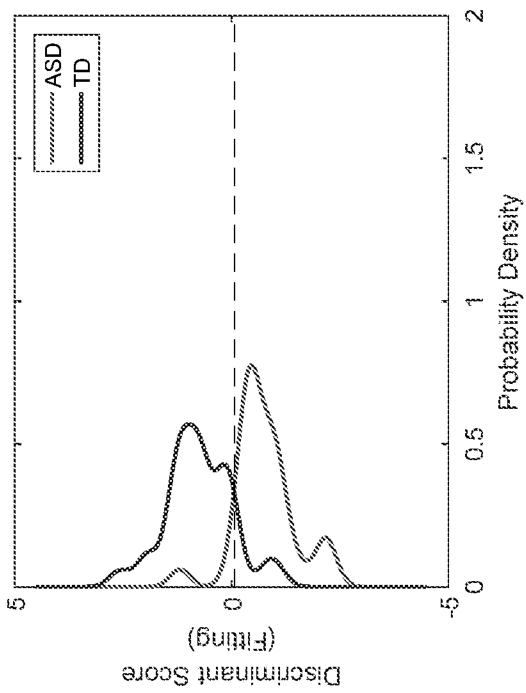
FIG. 2. Fitting results of the combination of serum metabolites 2,3-Dihydroxybenzoic acid, 2-Aminoadipic acid, 13C5-15N-Glutamic acid, Methylmalonic acid, and Levulinic acid.
Figure 2:
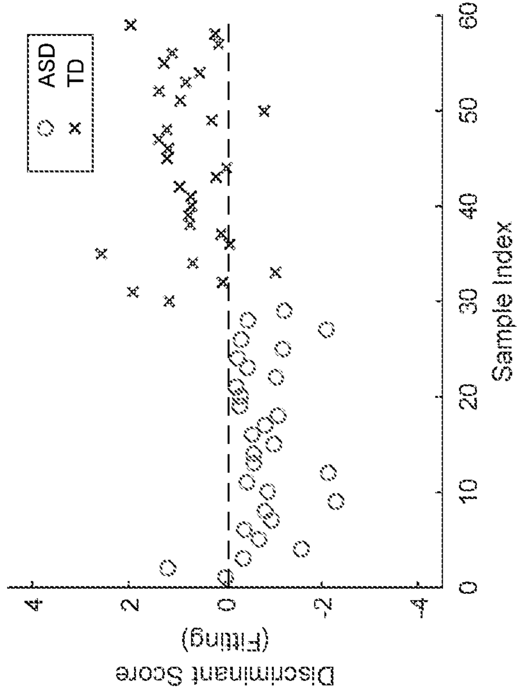
Figure 2:
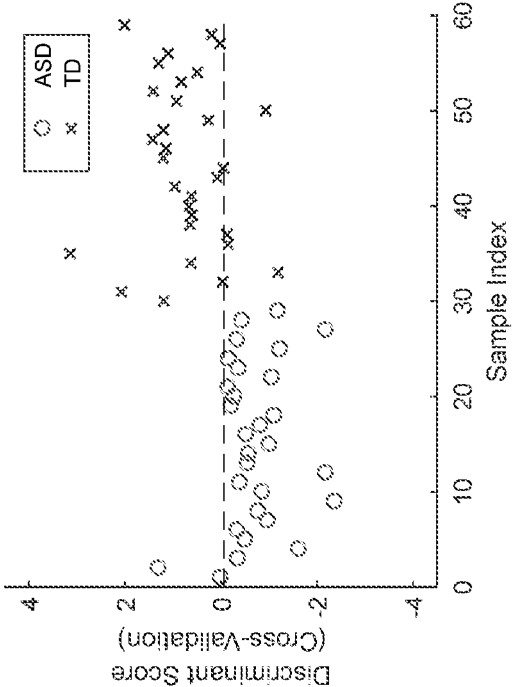
Figure 3:
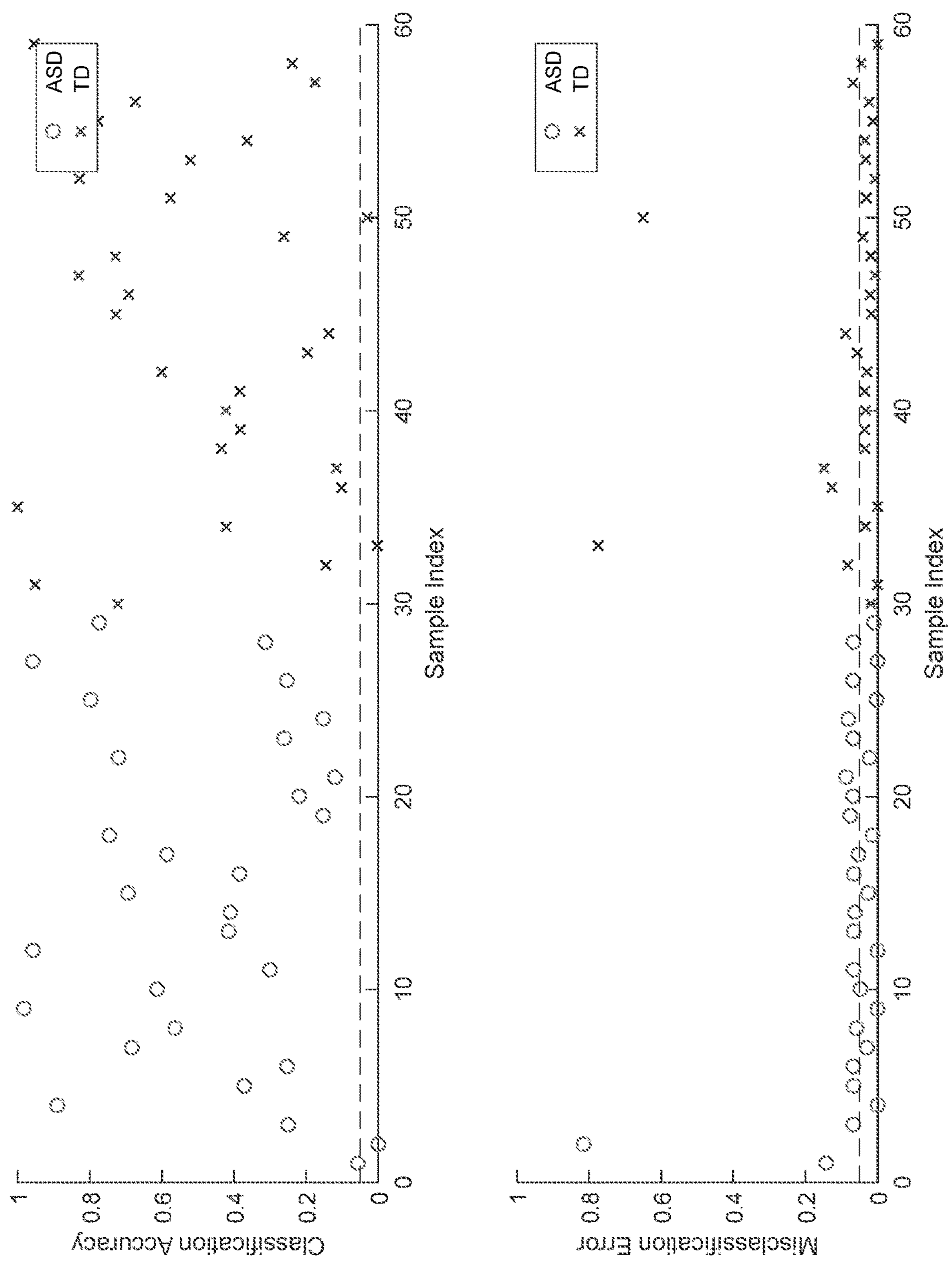
FIG. 3. Cross-validation of results in FIG. 2.

The classification accuracies and misclassification errors from cross-validation are shown in FIG. 2 and FIG. 3. Although a large number of samples have misclassification errors greater than 0.05, these values are just slightly greater than this cut-off and do not highlight any major concerns with the model.

Example 9. Multivariate Analysis of Autism-Urine-Analyzed Dataset

Initial multivariate analysis performed had indicated that the optimal five metabolite Fisher's Discriminant Analysis (FDA) model consisted of taurine, 4-Imidazoleacetic acid, xylose, phenylacetic acid and uracil. The metabolites taurine, 4-Imidazoleacetic acid, xylose, phenylacetic acid were present in a significant proportion of the top metabolite models.

Multivariate analysis was performed utilizing all urine metabolites that had demonstrated an AUROC value greater than 0.6, with creatine normalization. There were 97 such metabolites, which were subsequently considered Table 17.

TABLE 17

| Metabolite Name | AUROC |
|---|---|
| 4-Hydroxybenzoic acid Results | 0.625926 |
| Protocatechuic acid Results | 0.708642 |
| 2-Hydroxyphenylacetic acid/3-Hydroxyphenylacetic acid Results | 0.607407 |
| Adenosine Results | 0.676543 |
| Allopurinol Results | 0.67284 |
| Acetohydroxamic acid Results | 0.608642 |
| 2,3-Dihydroxybenzoic acid Results | 0.665432 |
| TMAO Results | 0.637037 |
| Methylmalonic acid Results | 0.654321 |
| Hippuric acid Results | 0.698765 |
| 13C3-Lactate Results | 0.644444 |
| Taurine Results | 0.720988 |
| Gentisic acid Results | 0.68642 |
| Guanine Results | 0.644444 |
| Phosphocreatine Results | 0.637037 |
| Glutamic acid Results | 0.650617 |
| Carnosine Results | 0.633333 |
| Imidazole Results | 0.611111 |
| Palmitic acid Results | 0.720988 |
| 4-Imidazoleacetic acid Results | 0.681481 |
| 2-Methylbutyric acid/Valeric acid Results | 0.624691 |
| Ribose Results | 0.610672 |
| Valine Results | 0.745679 |
| Xylose Results | 0.676543 |
| Glycine Results | 0.641975 |
| Betaine Results | 0.645679 |
| Erythrose Results | 0.616049 |
| 2-Deoxyadenosine Results | 0.617284 |
| 2-Methylglutaric acid Results | 0.624691 |
| Pyridoxine Results | 0.654321 |
| Glutamine Results | 0.64321 |
| Serine Results | 0.666667 |
| Urate Results | 0.630864 |
| Adenine Results | 0.645679 |
| 4-Methyl-2-oxopentanoic acid/Ketoleucine/ Ketoisoleucine Results | 0.61358 |
| Histidine Results | 0.62716 |
| Nonadecanoic acid Results | 0.65679 |
| Fructose/Galactose Results | 0.616049 |
| Uridine Results | 0.693827 |
| Phenylacetic acid Results | 0.67037 |
| Anthranilic acid Results | 0.625926 |
| Tyrosine Results | 0.680247 |
| Acetyl-L-glutamine Results | 0.622222 |
| Cytidine Results | 0.62716 |
| Glucose Results | 0.644444 |
| Neopterin Results | 0.67284 |
| Stearic acid Results | 0.616049 |
| 2-Pyrrolidinone Results | 0.660494 |
| 3-Methyl-2-oxovaleric acid Results | 0.679012 |
| Methyl alpha-D-glucopyranoside Results | 0.662963 |
| Picolinic acid Results | 0.667901 |
| 3-hydroxykynurenine Results | 0.633333 |
| Sucrose Results | 0.607407 |
| Methylhistamine Results | 0.646914 |
| Ferulic acid Results | 0.711111 |
| dTMP Results | 0.702469 |
| cGMP Results | 0.650617 |
| NAD Results | 0.634568 |
| 4-Pyridoxic acid Results | 0.674074 |
| Xanthurenic acid Results | 0.72716 |
| Adenosyl-L-homocysteine Results | 0.601235 |
| Proline Results | 0.712346 |
| Sebacic acid Results | 0.608642 |
| Xanthosine Results | 0.618519 |
| 5-Hydroxytryptophan Results | 0.749383 |
| Acetylornithine Results | 0.650617 |
| pregnenolone sulfate Results | 0.661728 |
| L-Ascorbic acid Results | 0.698765 |
| Melatonin Results | 0.681481 |
| Decanoylcarnitine Results | 0.674074 |
| Raffinose Results | 0.62963 |
| GA3P Results | 0.683951 |
| Kynurenic acid Results | 0.606173 |
| 6-Hydroxynicotinic acid Results | 0.630864 |
| G16BP Results | 0.695062 |
| belta-Hydroxyisovaleric acid Results | 0.614815 |
| 2-hydroxybutyric acid/Malonic acid Results | 0.611111 |
| Acetamide Results | 0.614815 |
| p-Coumaric acid Results | 0.651852 |
| N-Acetylneuraminic acid Results | 0.687654 |
| 13C5-15N-Glutamic acid Results | 0.603704 |
| Ethylmalonic acid Results | 0.616049 |
| G1P Results | 0.601235 |
| Glutathione oxidized Results | 0.733333 |
| Mucic acid Results | 0.642857 |
| UDP Results | 0.767901 |
| DUMP Results | 0.657967 |
| Levulinic acid Results | 0.62963 |
| F16BP Results | 0.633333 |
| Pyruvate Results | 0.614304 |
| Tryptamine Results | 0.625926 |
| Shikimic acid Results | 0.641975 |
| Homovanillic acid Results | 0.623457 |
| Dimethylarginine Results | 0.61358 |
| Uracil Results | 0.612346 |
| Propranolol Results | 0.603704 |
| Folic acid Results | 0.607407 |

For the initial model discovery step, all possible combinations of four from among these 97 metabolites were evaluated using FDA. Those models that achieved an AUROC value greater than 0.92 were then used to determine an optimal five-metabolite model.

Five-metabolite model discovery involved augmenting each of the four-metabolite models with all possible combinations of the remaining 93 metabolites. In total, 1,829 models were able to achieve an AUROC greater than 0.94. Models that had achieved this metric were then subjected to leave-one-out cross validation. The models that achieved the highest accuracy after cross-validation are shown in Table 18.

TABLE 18

| Variable Combination | Fitted AUROC | Cross validation Accuracy |
|---|---|---|
| Taurine<br>Palm itic acid<br>4-Imidazoleacetic acid<br>deoxythymidine monophosphate<br>Shikimic acid | 0.97 | .96 |
| Taurine<br>Imidazole<br>4-Imidazoleacetic acid<br>deoxythymidine monophosphate<br>Sebacic acid | 0.95 | .96 |
| Taurine<br>4-Imidazoleacetic acid<br>deoxythymidine monophosphate<br>Sebacic acid<br>5-Hydroxytryptophan | 0.96 | .95 |

What is claimed is:

1. A method of treating Autism Spectrum Disorder (ASD) in a subject suspected of having or at risk of having ASD, the method comprising:

(a) in a biological sample obtained from the subject, measuring or having measured a level of each of at least two metabolites in combination wherein the at least two metabolites in combination are selected from the group consisting of: 4-Hydroxy-3-methylbenzoic acid and Tryptamine; and 4-Hydroxy-3-methylbenzoic acid and 5-Hydroxytryptophan;

(b) comparing the measured level of each metabolite in the selected combination against a control metabolite level for each metabolite, wherein the control level for each metabolite is determined by measuring a metabolite level in a control, typically developing (TD) subject, wherein the comparing comprises calculating the Type I false positive rate (FPR) and Type II false negative rate (FNR) errors for the selected combination of metabolites using Fisher's Discriminant Analysis (FDA) or logistic regression;

(c) indicating the subject as having or at risk of ASD when, for the selected combination, the Type I error is about or below 20%, and the Type II error is about or below 20%; and (d) administering to the subject identified as having or at risk of ASD, a treatment selected from the group consisting of:

(i) a medication selected from an antipsychotic drug, a selective serotonin re-uptake inhibitor (SSRI), a tricyclic, a psychoactive or anti-psychotic medication, a stimulant, an anti-anxiety medication, or an anticonvulsant;

(ii) a nutritional supplementation; and (iii) a composition comprising fecal microbiota from a healthy neurotypical human donor.

2. The method of claim 1, wherein step (a) comprises preparing a sample extract from the biological sample and obtaining the level of each metabolite in the combination of at least two metabolites in the sample extract using Ultrahigh Performance Liquid Chromatography-Tandem Mass Spectroscopy (UPLC-MS/MS).

3. The method of claim 1, wherein the method determines the subject as having or at risk of ASD at birth or pre-birth.

4. The method of claim 1, wherein the biological sample is a urine sample.

5. The method of claim 4, wherein the two metabolites are 4-Hydroxy-3-methylbenzoic acid and Tryptamine.

6. The method of claim 1, wherein the biological sample is serum.

7. The method of claim 1, wherein the treatment is further personalized for the subject determined as having or at risk of having ASD.

8. The method of claim 1, further comprising measuring a level of each of at least two metabolites in combination wherein the at least two metabolites in combination are selected from the group consisting of: 4-Hydroxy-3-methylbenzoic acid and Picolinic acid; 6-Hydroxynicotinic acid and Picolinic acid; 4-Hydroxy-3-methylbenzoic acid and Ethylmalonic acid; Mannose and 4-Hydroxy-3-methylbenzoic acid; Acetylglucosamine and 4-Hydroxy-3-methylbenzoic acid; Glutaric acid and 4-Hydroxy-3-methylbenzoic acid; Tyrosine and 4-Hydroxy-3-methylbenzoic acid; Nicotinamide and 4-Hydroxy-3-methylbenzoic acid; 4-Hydroxy-3-methylbenzoic acid and 2-Aminoadipic acid; Glutamine and 4-Hydroxy-3-methylbenzoic acid; Tyrosine and Nicotinamide; Kynurenic acid and 4-Hydroxy-3-methylbenzoic acid; Glutaric acid and Tryptamine; and Gentisic acid and 4-Hydroxy-3-methylbenzoic acid.

9. A method of treating Autism Spectrum Disorder (ASD) in a subject suspected of having or at risk of having ASD, the method comprising: administering to the subject a treatment, wherein the subject has been determined as having or at risk of ASD by having a Type I error of about or below 20%, and a Type II error of about or below 20% for a level of each of two metabolite in a selected combination of at least two metabolites in a biological sample obtained from the subject, wherein two metabolites in combination are selected from the group consisting of: 4-Hydroxy-3-methylbenzoic acid and Tryptamine; and 4-Hydroxy-3-methylbenzoic acid and 5-Hydroxytryptophan; and wherein the treatment is selected from:

(i) a medication selected from an antipsychotic drug, a selective serotonin re-uptake inhibitor (SSRI), a tricyclic, a psychoactive or anti-psychotic medication, a stimulant, an anti-anxiety medication, or an anticonvulsant;

(ii) a nutritional supplementation; and (iii) a composition comprising fecal microbiota from a healthy neurotypical human donor.

10. The method of claim 9, wherein the level of each metabolite is obtained from a sample extract prepared from the biological sample using Ultrahigh Performance Liquid Chromatography-Tandem Mass Spectroscopy (UPLC-MS/MS).

11. The method of claim 9, wherein the subject is determined as having or at risk of ASD at birth or pre-birth.

12. The method of claim 9, further comprising measuring a level of each of at least two metabolites in combination wherein the at least two metabolites in combination are selected from the group consisting of: 4-Hydroxy-3-methylbenzoic acid and Picolinic acid; 6-Hydroxynicotinic acid and Picolinic acid; 4-Hydroxy-3-methylbenzoic acid and Ethylmalonic acid; Mannose and 4-Hydroxy-3-methylbenzoic acid; Acetylglucosamine and 4-Hydroxy-3-methylbenzoic acid; Glutaric acid and 4-Hydroxy-3-methylbenzoic acid; Tyrosine and 4-Hydroxy-3-methylbenzoic acid; Nicotinamide and 4-Hydroxy-3-methylbenzoic acid; 4-Hydroxy-3-methylbenzoic acid and 2-Aminoadipic acid; Glutamine and 4-Hydroxy-3-methylbenzoic acid; Tyrosine and Nicotinamide; Kynurenic acid and 4-Hydroxy-3-methylbenzoic acid; Glutaric acid and Tryptamine; and Gentisic acid and 4-Hydroxy-3-methylbenzoic acid.

* * * * *